US009289500B2

(12) United States Patent
Guan et al.

(10) Patent No.: US 9,289,500 B2
(45) Date of Patent: Mar. 22, 2016

(54) SACCHARIDE-PEPTIDE HYDROGELS

(71) Applicants: The Regents of the University of California, Oakland, CA (US); City of Hope, Duarte, CA (US)

(72) Inventors: Zhibin Guan, Irvine, CA (US); Yoko Mullen, Sherman Oaks, CA (US); Sophia W. Liao, Irvine, CA (US)

(73) Assignees: The Regents of the University of California, Oakland, CA (US); City of Hope, Duarte, CA (US)

( * ) Notice: Subject to any disclaimer, the term of this patent is extended or adjusted under 35 U.S.C. 154(b) by 0 days.

(21) Appl. No.: 14/186,973

(22) Filed: Feb. 21, 2014

(65) Prior Publication Data

US 2014/0242123 A1    Aug. 28, 2014

Related U.S. Application Data

(60) Provisional application No. 61/768,372, filed on Feb. 22, 2013.

(51) Int. Cl.
| | |
|---|---|
| *A61K 9/00* | (2006.01) |
| *A61K 47/42* | (2006.01) |
| *A61K 47/26* | (2006.01) |
| *A61K 9/06* | (2006.01) |
| *A61K 47/48* | (2006.01) |

(52) U.S. Cl.
CPC .............. *A61K 47/42* (2013.01); *A61K 9/0024* (2013.01); *A61K 9/06* (2013.01); *A61K 47/26* (2013.01); *A61K 47/4823* (2013.01); *A61K 47/48192* (2013.01); *A61K 47/48784* (2013.01)

(58) Field of Classification Search
None
See application file for complete search history.

(56) References Cited

U.S. PATENT DOCUMENTS

| | | | |
|---|---|---|---|
| 8,207,234 B1* | 6/2012 | Rodgers et al. | 514/6.9 |
| 2005/0074497 A1* | 4/2005 | Schultz | 424/486 |
| 2014/0010862 A1* | 1/2014 | Sinko | A61F 6/04 424/450 |
| 2014/0288190 A1* | 9/2014 | Ashley | A61K 47/48215 514/772.3 |
| 2014/0341842 A1* | 11/2014 | Zarembinski | A61K 47/36 424/85.1 |

OTHER PUBLICATIONS

Guignard et al. Cost Analysis of Human Islet Transplantation for the Treatment of Type 1 Diabetes in the Swiss-French Consortium GRAGIL. Diabetes Care, 2004. vol. 27, No. 4, pp. 895-900.*
Weber et al. Hydrogel encapsulation environments functionalized with extracellular matrix interactions increase islet insulin secretion. Matrix Biol. 2008. vol. 27, No. 8, pp. 667-673.*
Solari et al. Marginal Mass islet transplantation with autologoous mesenchymal stem cells promotes long-term islet allograft survival and sustained normoglycemia. Journal of Autoimmunity, 2009. vol. 32, pp. 116-124.*
Pitarresi et al. Photocrosslinking of dextran and polyaspartamide derivatives: A combination suitable for colon-specific drug delivery. J Controlled Release, 2007, vol. 119, pp. 328-338.*
Sengupta et al. Alternate glucocorticoid receptor ligand binding structures influence outcomes in an in vivo tissue regeneration model. Com Biochem Physiol C Toxicol Pharmacol, Aug. 2012, vol. 156, No. 2, pp. 121-129.*
Metters et al., Network formation and degradation behavior of hydrogels formed by Michael-type addition reactions Biomacromolecules 6:290-301 (2005).
Metzke et al. A novel carbohydrate-derived side-chain polyether with excellent protein resistance. J. Am. Chem. Soc. 125:7760-7761 (2003).
Metzke et al., Structure-property studies on carbohydrate-derived polymers for use as protein-resistant biomaterials. Biomacromolecules 9:208-215 (2008).
Negishi et al., Luminescence technology in preservation and transplantation for rat islet. Islets 2011;3:111e7 (2011).
Nie et al., Production of heparin-containing hydrogels for modulating cell responses. Acta Biomater. 5:865-875 (2009).
Nikolova et al., The vascular basement membrane: a niche for insulin gene expression and beta cell proliferation. Dev Cell 10:397e405 (2006).
Nuttelman et al., Macromolecular monomers for the synthesis of hydrogel niches and their application in cell encapsulation and tissue engineering Prog. Polym. Sci. 33: 167-179 (2008).
Omori et al., Microassay for glucose-induced preproinsulin mRNA expression to assess islet functional potency for islet transplantation. Transplantation 89:146e54 (2010).
Paszek et al., Tensional homeostasis and the malignant phenotype. Cancer Cell 8:241-254 (2005).
Peppas et al., Hydrogels in biology and medicine: from molecular principles to bionanotechnology AdV. Mater. 18:1345-1360 (2006).
Rackham et al., Co-transplantation of mesenchymal stem cells maintains islet organisation and morphology in mice. Diabetologia 54:1127-1135 (2011).
Reed et al., In situ mechanical interferometry of matrigel films. Langmuir 25:36-39 (2009).
Rehfeldt et al., Cell responses to the mechanochemical microenvironment—implications for regenerative medicine and drug delivery. AdV. Drug DeliVery ReV. 59:1329-1339 (2007).
Rizzi et al., Recombinant protein-co-PEG networks as cell-adhesive and proteolytically degradable hydrogel matrixes. Part I: Development and physicochemical characteristics. Biomacromolecules 6:1226-1238 (2005).
Salvay et al., Extracellular matrix protein-coated scaffolds promote the reversal of diabetes after extrahepatic islet transplantation. Transplantation 85:1456e64 (2008).

(Continued)

*Primary Examiner* — Marcela M Cordero Garcia
(74) *Attorney, Agent, or Firm* — Joseph R. Baker, Jr.; Gavrilovich, Dodd & Lindsey LLP

(57) ABSTRACT

The disclosure provides for saccharide-peptide based hydrogels, the functionalization of the saccharide-peptide based hydrogels with one or more biological agents, and the encapsulation of one or more biological materials and/or pharmaceutical agents in the hydrogels. The disclosure further provides for the use of the saccharide-peptide based hydrogels in treating a disease or disorder in a subject.

30 Claims, 15 Drawing Sheets

(56) References Cited

OTHER PUBLICATIONS

Schense et al., Cross-linking exogenous bifunctional peptides into fibrin gels with factor XIIIa. Bioconjugate Chem. 10:75-81 (1999).
Seliktar D. Designing cell-compatible hydrogels for biomedical applications. Science 336:1124e8 (Jun. 15, 2012).
Silva et al., Selective differentiation of neural progenitor cells by high-epitope density nanofibers. Science 303:1352-1355 (2004).
Solon et al. Fibroblast adaptation and stiffness matching to soft elastic substrates. Biophys. J. 93:4453-4461 (2007).
Soofi et al., The elastic modulus of Matrigel as determined by atomic force microscopy. J. Struct. Biol. 167:216-219 (2009).
Stendahl et al., Extracellular matrix in pancreatic islets: relevance to scaffold design and transplantation. Cell Transplant 18:1e12 (2009).
Su et al., Anti-inflammatory peptide-functionalized hydrogels for insulin-secreting cell encapsulation. Biomaterials 31:308e14 (2010).
Tan et al., Thermosensitive injectable hyaluronic acid hydrogel for adipose tissue engineering. Biomaterials 30 (36):6844-6853 (2009).
Tibbet et al., Hydrogels as Extracellular Matrix Mimics for 3D Cell Culture. Biotechnol Bioeng. 103(4):655-663 (2009).
Toyofuku et al., Natural killer T-cells participate in rejection of islet allografts in the liver of mice. Diabetes 55:34e9 (2006).
Urakami et al.,Living Ring-Opening Polymerization of a Carbohydrate-Derived Lactone for the Synthesis of Protein-Resistant Biomaterials. Biomacromolecules, Jan. 26, 2008, 9, 592-597.
Vercruysse et al. Synthesis and in vitro degradation of new polyvalent hydrazide cross-linked hydrogels of hyaluronic acid. Bioconjugate Chem. 8:686-694 (1997).
Wang et al. Substrate flexibility regulates growth and apoptosis of normal but not transformed cells. Am. J. Physiol. Cell Physiol. 279:C1345-1350 (2000).
Weber et al., Cell-matrix interactions improve Beta-cell survival and insulin secretion in three-dimensional culture. Tissue Eng Part A 14:1959e68 (2008).
Yamaguchi et al., Growth Factor Mediated Assembly of Cell Receptor-Responsive Hydrogels J. Am. Chem. Soc. 129:3040-3041 (2007).
Akinc et al., "A combinatorial library of lipid-like materials for delivery of RNAi therapeutics," Nat Biotechnol 26:561-569 (2008).
Barnard et al., Degradable Self-Assembling Dendrons for Gene Delivery: Experimental and Theoretical Insights into the Barriers to Cellular Uptake J Am Chem Soc 133:20288-20300 (2011).
Behr, J. P., "Synthetic Gene Transfer Vectors II: Back to the Future," Acc Chem Res 45:980-984 (Feb. 2012).
Burnett et al., "RNA-based Therapeutics—Current Progress and Future Prospects," J. Chem Biol 19:60-71 (Jan. 2012).
Chen et al., "Bioreducible Hyperbranched Poly(amido amine)s for Gene Delivery," Biomacromolecules 10:2921-2927 (2009).
Creusat et al., "Self-Assembling Polyethylenimine Derivatives Mediate Efficient siRNA Delivery in Mammalian Cells," Chembiochem 9:2787-2789 (2008).
Crombez et al., "Targeting cyclin B1 through peptide-based delivery of siRNA prevents tumour growth," Nucleic Acids Res 37(14):4559-4569 (2009).
Cui et al., "Conjugation Chemistry through Acetals toward a Dextran-Based Delivery System for Controlled Release of siRNA," J Am Chem Soc 134:15840 (Sep. 2012).
Davis et al., "Evidence of RNAi in humans from systemically administered siRNA via targeted nanoparticles," Nature 464:1067-1071 (2010).
Dunn et al., "Reductively-responsive siRNA-conjugated hydrogel nanoparticles for gene silencing," J Am Chem Soc 134:7423-7430 (May 2012).
Fischer et al., "Dendritic Polyglycerols with Oligoamine Shells Show Low Toxicity and High siRNA Transfection Efficiency in Vitro," Bioconjug Chem 21:1744-1752 (2010).
Kim et al., "Polyoxalate Nanoparticles as a Biodegradable and Biocompatible Drug Delivery Vehicle," Biomacromolecules 11: 555-560 (2010).
Kim et al., "Dendronized gold nanoparticles for siRNA delivery," Small 8:3253-3256 (Nov. 2012).
Kulkarni et al., "Pendant Polymer:Amino-β-Cyclodextrin:siRNA Guest:Host Nanoparticles as Efficient Vectors for Gene Silencing," J Am Chem Soc 134:7596-7599 (Apr. 30, 2012).
Liu et al., "SiRNA Delivery Systems Based on Neutral Cross-Linked Dendrimers," Bioconjug Chem 23:174-183 (Jan. 2012).
Liu et al., "Efficient Delivery of Sticky siRNA and Potent Gene Silencing in aProstate Cancer Model Using a Generation 5 Triethanolamine-Core PAMAM Dendrimer," Mol Pharmaceutics 9:470-481 (Mar. 2012).
Merkel et al., "Molecular modeling and in vivo imaging can identify successful flexible triazine dendrimer-based siRNA delivery systems," J Control Release 153(1):23-33 (2011).
Nguyen et al., "Polymeric Materials for Gene Delivery and DNA Vaccination," Adv Mater 21:847-867 (2009).
Nguyen et al., "Nucleic acid delivery: the missing pieces of the puzzle?," Acc Chem Res 45:1153-1162 (Jul. 2012).
Pavan et al., "Computational Insights into the Interactions between DNA and siRNA with "Rigid" and "Flexible" Triazine Dendrimers," Biomacromolecules 11: 721-730 (2010).
Pavan et al., "Dendrimers and dendrons for siRNA binding: computational insights," J Drug Deliv Sci Tec 22:83-89 (2012).
Rajeswari et al., "Does Tryptophan Intercalate in DNA? A Comparative Study of Peptide Binding to Alternating and Nonalternating A*T Sequences," Biochemistry 26:6825-6831 (1987).
Rettig et al., "Progress Toward In Vivo Use of siRNAs-II," Mol Ther 20:483-512 (Mar. 2012).
Schafer et al., "Redox environment of the cell as viewed through the redox state of the glutathione disulfide/glutathione couple," Free Rad. Biol. Med. 30:1191-1212 (2001).
Schaffer et al., "Molecular Engineering of Viral Gene Delivery Vehicles," Annu Rev Biomed Eng 10:169-194 (2008).
Smith et al., "Diblock Glycopolymers Promote Colloidal Stability of Polyplexes and Effective pDNA and siRNA Delivery under Physiological Salt and Serum Conditions," Biomacromolecules 12:3015-3022 (2011).
Son et al., "Bioreducible Polymers for Gene Silencing and Delivery," J. Acc Chem Res 45:1100-1112 (2011).
Sonawane et al., "Chloride Accumulation and Swelling in Endosomes Enhances DNA Transfer by Polyamine-DNA Polyplexes," J Biol Chem 278:44826-44831 (2003).
Tang et al., "In Vitro Gene Delivery by Degraded Polyamidoamine Dendrimers," Bioconjugate Chem 7:703-714 (1996).
Wagner, E., "Polymers for siRNA Delivery: Inspired by Viruses to be Targeted, Dynamic, and Precise," Acc Chem Res 45:1005-1013 (2011).
Wakefield et al., "Membrane Activity and Transfection Ability of Amphipathic Polycations as a Function of Alkyl Group Size," Bioconjug Chem 16:1204-1208 (2005).
Ashcroft et al., Glucose metabolism in mouse pancreatic islets. Biochem J 118:143e54 (1970).
Banerjee et al. The influence of hydrogel modulus on the proliferation and differentiation of encapsulated neural stem cells. Biomaterials 30:4695-4699 (2009).
Banwell et al., Rational design and application of responsive alpha-helical peptide hydrogels. Nat. Mater. 8:596-600 (2009).
Bennet et al., Incompatibility between human blood and isolated islets of Langerhans: a finding with implications for clinical intraportal islet transplantation? Diabetes 48:1907e14 (1999).
Blomeier et al. Polymer scaffolds as synthetic microenvironments for extrahepatic islet transplantation. Transplantation 82:452e9 (2006).
Borg et al., The use of biomaterials in islet transplantation. Curr Diab Rep 11:434e44 (2011).
Brown et al. Importance of hepatic portal circulation for insulin action in streptozotocin-diabetic rats transplanted with fetal pancreases. J Clin Invest 64:1688e94 (1979).
Bryant et al., Hydrogel properties influence ECM production by chondrocytes photoencapsulated in poly(ethylene glycol) hydrogels. J. Biomed. Mater. Res. 59:63-72 (2002).
Bryant et al., Incorporation of tissue-specific molecules alters chondrocyte metabolism and gene expression in photocrosslinked hydrogels. Acta Biomater. 1:243-252 (2005).

(56) References Cited

OTHER PUBLICATIONS

Burdick et al. Photoencapsulation of osteoblasts in injectable RGD-modified PEG hydrogels for bone tissue engineering Biomaterials 23:4315-4323 (2002).
Burdick et al. Controlled degradation and mechanical behavior of photopolymerized hyaluronic acid networks. Biomacromolecules 6:386-391 (2005).
Carlsson et al., Markedly decreased oxygen tension in transplanted rat pancreatic islets irrespective of the implantation site. Diabetes 50:489e95 (2001).
Chawla et al., Biodegradable and biocompatible synthetic saccharide-Peptide hydrogels for three-dimensional stem cell culture. Biomacromolecules 12:560e7 (2011).
Chawla et al., Modulation of chondrocyte behavior through tailoring functional synthetic saccharide-peptide hydrogels. Biomaterials 33:6052e60 (Sep. 1, 2012).
Deforest et al., S. Sequential click reactions for synthesizing and patterning three-dimensional cell microenvironments. Nat. Mater. 8:659-664 (2009).
Degoricija et al., Hydrogels for osteochondral repair based on photocrosslinkable carbamate dendrimers. Biomacromolecules 9:2863-2872 (2008).
Discher et al., Tissue cells feel and respond to the stiffness of their substrate. Science 310:1139-1143 (2005).
Drury et al., Hydrogels for tissue engineering: scaffold design variables and applications. J. Biomaterials 24:4337-4351 (2003).
Economic costs of diabetes in the U.S. in 2007. Diabetes Care 31:596e 615 (2008).
Elbert et al., Conjugate addition reactions combined with free-radical cross-linking for the design of materials for tissue engineering. Biomacromolecules 2:430-441 (2001).
Engler et al., Matrix elasticity directs stem cell lineage specification. Cell 126:677-689 (2006).
Flanagan et al., Neurite branching on deformable substrates. NeuroReport 13: 2411-2415 (2002).
Frisch et al., Anoikis mechanisms. Curr Opin Cell Biol 13:555e62 (2001).
Gelain et al., Designer self-assembling peptide nanofiber scaffolds for adult mouse neural stem cell 3-dimensional cultures. S. PLoS One 1:e119 (2006).
Grieshaber et al., Synthesis and Characterization of Elastin-Mimetic Hybrid Polymers with Multiblock, Alternating Molecular Architecture and Elastomeric Properties. Macromolecules 42:2532-2541(2009).
Guilak et al., Control of stem cell fate by physical interactions with the extracellular matrix. Cell Stem Cell 5, 17-26 (2009).
Haines-Butterick et al., Controlling hydrogelation kinetics by peptide design for three-dimensional encapsulation and injectable delivery of cells. Proc. Natl. Acad. Sci. U.S.A. 104:7791-7796 (2007).
Hiemstra et al., Rapidly in situ forming biodegradable robust hydrogels by combining stereocomplexation and photopolymerization. J. Am. Chem. Soc. 129:9918-9926 (2007).
Hu et al., Rational design of transglutaminase substrate peptides for rapid enzymatic formation of hydrogels. J. Am. Chem. Soc. 125, 14298-14299 (2003).
Hu et al., Hydrogels cross-linked by native chemical ligation. Biomacromolecules 2194-2200 (2009).
Hwang et al., Cartilage tissue engineering: Directed differentiation of embryonic stem cells in three-dimensional hydrogel culture. J. Methods Mol. Biol. 407:351-373 (2007).
Ingber et al., Cell structure and hierarchical systems biology. J. Cell Sci. 116:1157-1173 (2003).
Inukai et al., Preparation and characterization of hyaluronate-hydroxyethyl acrylate blend hydrogel for controlled release device. Chem. Pharm. Bull. 48:850-854 (2000).
Jun et al., Biomimetic self-assembled nanofibers Soft Matter 2:177-181 (2006).
Kersey et al., A hybrid polymer gel with controlled rates of cross-link rupture and self-repair J. R. Soc. Interface 4:373-380 (2007).
Kleinman et al., Isolation and characterization of type IV procollagen, laminin, and heparan sulfate proteoglycan from the EHS sarcoma. Biochemistry 21:6188-6193 (1982).
Kopecek, Hydrogel Biomaterials: A Smart Future? J. Biomaterials 28:5185-5192 (2007).
Lee et al., Controlling Mechanical and Swelling Properties of Alginate Hydrogels Independently by Cross-Linker Type and Cross-Linking Density Macromolecules 33, 4291-4294 (2000).
Lee et al., Hydrogels for tissue engineering. J. Chem ReV 101:1869-1879 (2001).
Lee et al. Three-dimensional micropatterning of bioactive hydrogels via two-photon laser scanning photolithography for guided 3D cell migration. Biomaterials 29:2962-2968 (2008).
Lee et al., Growth factor delivery-based tissue engineering: general approaches and a review of recent developments. J R Soc Interface 8:153e70 (2011).
Liao et al., De novo design of saccharide-peptide hydrogels as synthetic scaffolds for tailored cell responses. J Am Chem Soc 131:17638e46 (2009).
Liao et al., Maintaining functional islets through encapsulation in an injectable saccharide-peptide hydrogel. Biomaterials 34(16):3984-91 (Mar. 7, 2013).
Liao et al., The effect of cell-matrix interaction on encapsulated human islets. presented at the Congress of the International Pancreas and Islet Transplantation, (Jun. 2013).
Lin et al., PEG Hydrogels for the Controlled Release of Biomolecules in Regenerative Medicine Pharmacol. Res. 26:631-643 (2009).
Lin et al., Glucagon-like peptide-1 functionalized PEG hydrogels promote survival and function of encapsulated pancreatic beta-cells. Biomacromolecules 10:2460e7 (2009).
Lutolf et al., Synthesis and physicochemical characterization of end-linked poly(ethylene glycol)-co-peptide hydrogels formed by Michael-type addition. Biomacromolecules 4:713-722 (2003).
Martens et al., Tailoring the degradation of hydrogels formed from multivinyl poly(ethylene glycol) and poly(vinyl alcohol) macromers for cartilage tissue engineering. Biomacromolecules 4:283-292 (2003).
Martin et al., Human embryonic stem cells express an immunogenic nonhuman sialic acid. Nat Med 11:228e32 (2005).
McCall et al., Update on islet transplantation. Cold Spring Harb Perspect Med 2:a007823 (2012).
Ito et al., "Mesechymal Stem Cell and Islet Co-Transplantation Promotes Graft Revascularization and Function", Transplantation, 89(12):1438-1445 (Jun. 28, 2010).
Liao et al., "The Effect of Cell-Matrix Interaction on Encapsulated Human Islets," Transplantation 96(65):S97 (Sep. 27, 2013).
Moassesfar et al., Slide on Transplantation Medical Cost, Islets vs. Pancreas, presented before the International Pancreas & Islet Transplant Association (IPITA) Congress on Sep. 25, 2013.

\* cited by examiner

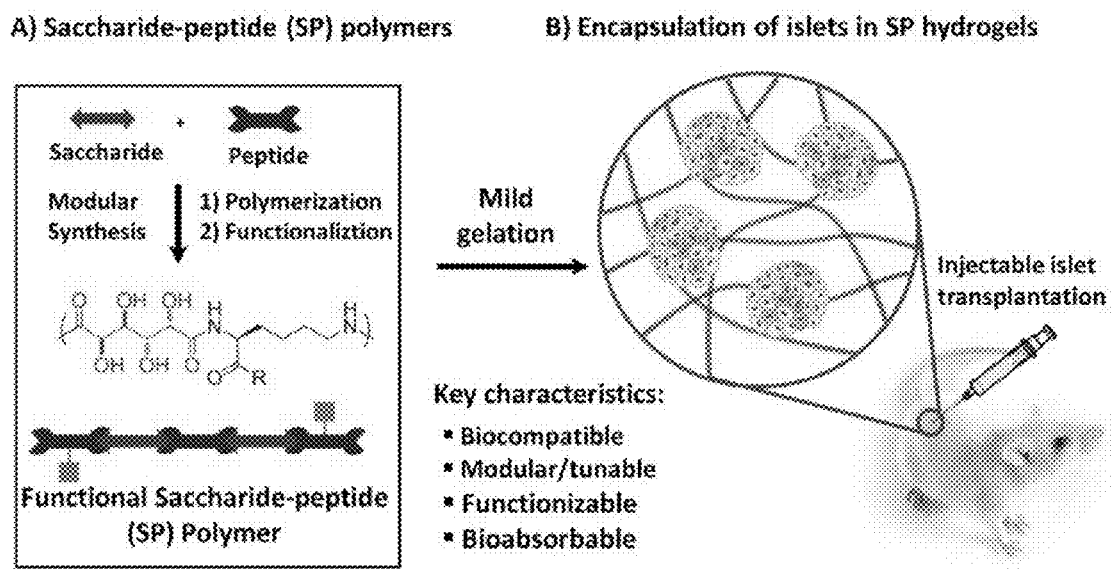
FIGURE 1A-B

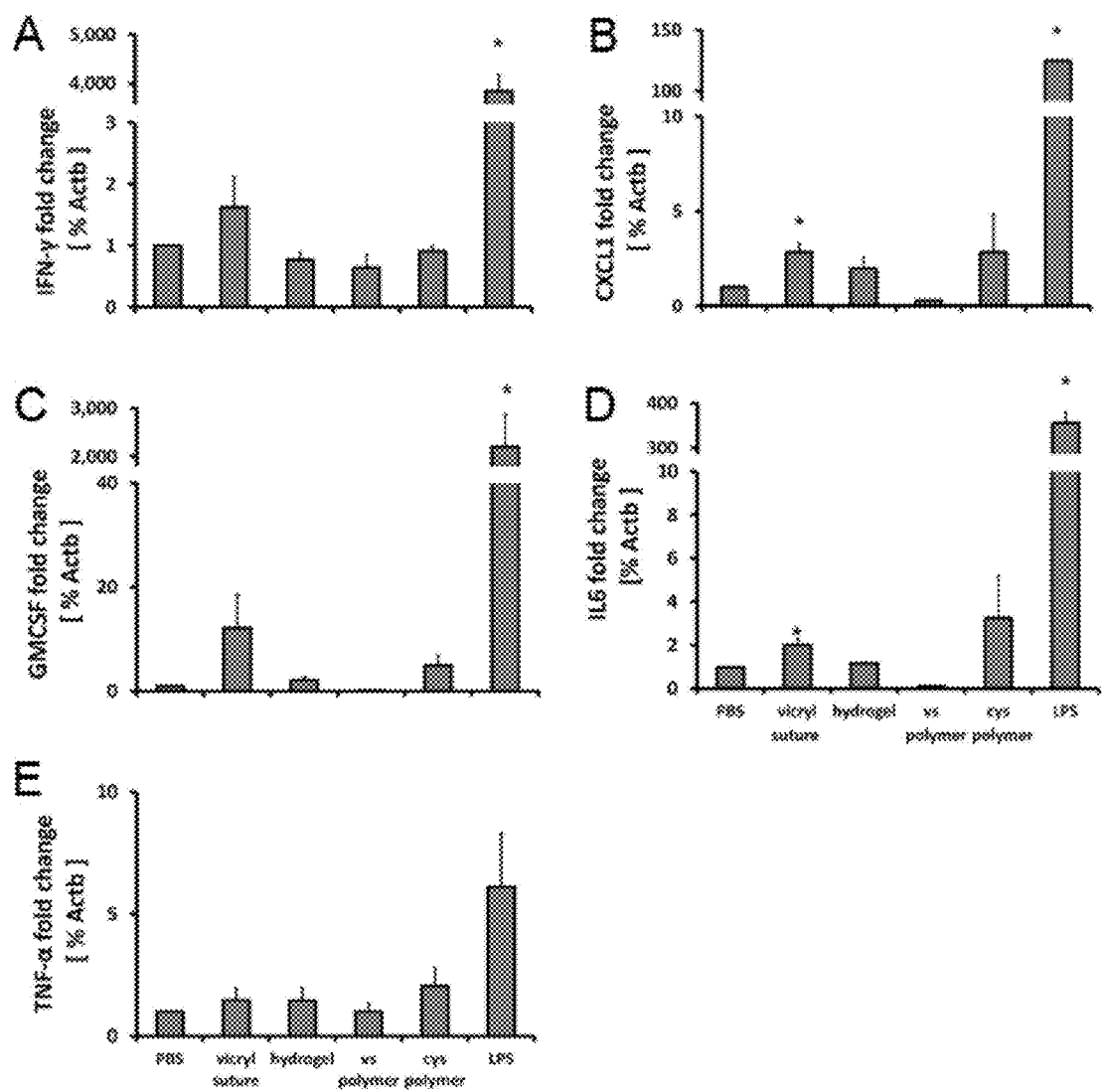
FIGURE 2A-E

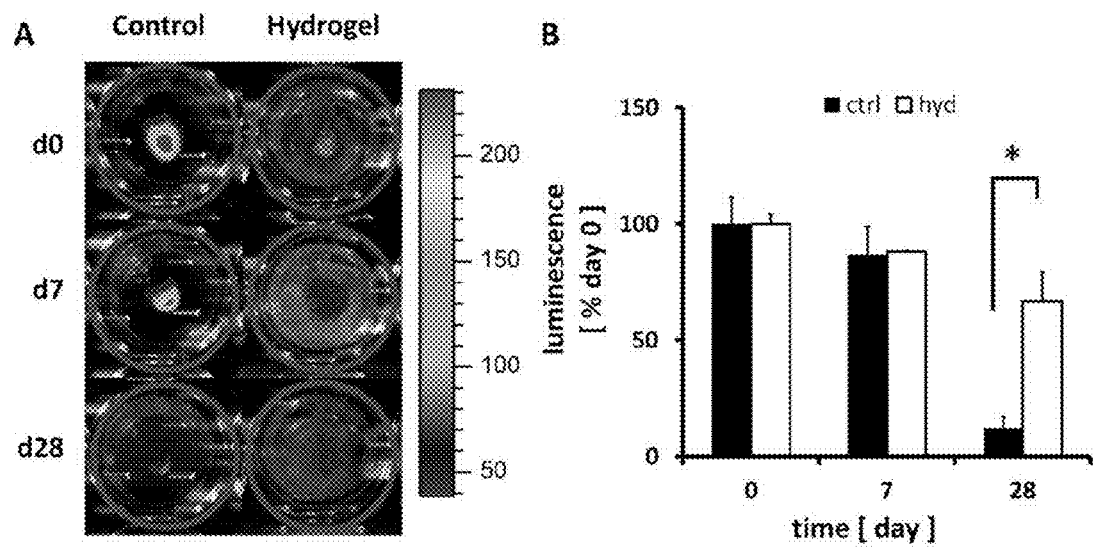
FIGURE 3A-B
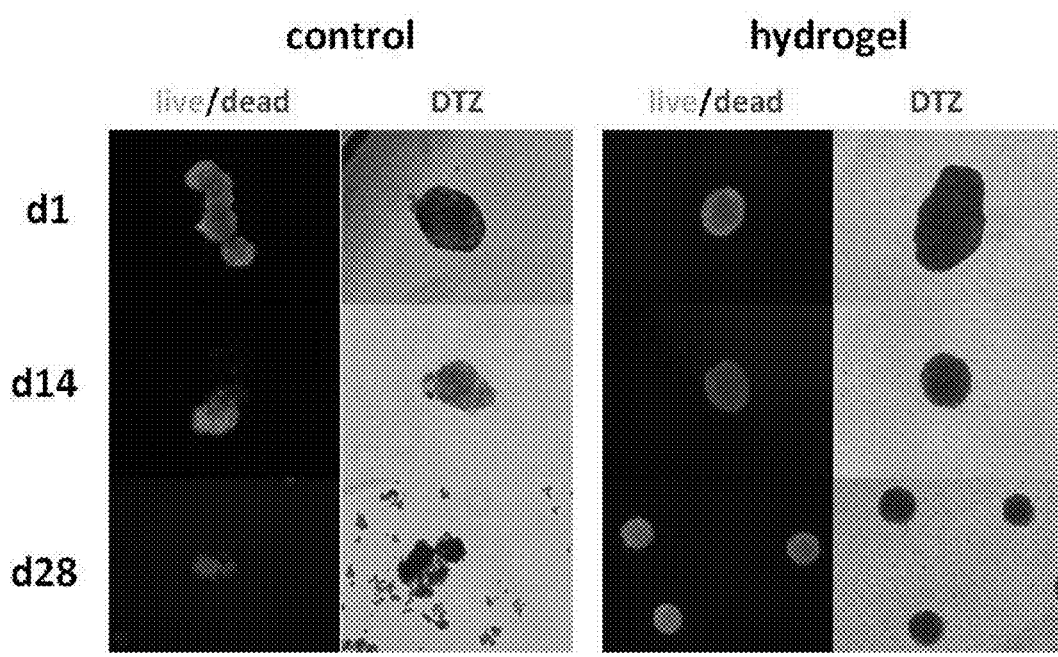
FIGURE 4

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Laminin Peptide

<400> SEQUENCE: 1

Ile Lys Val Ala Val
1               5

<210> SEQ ID NO 2
<211> LENGTH: 18
<212> TYPE: PRT
<213> ORGANISM: Artificial Sequence
<220> FEATURE:
<223> OTHER INFORMATION: Collagen IV Peptide

<400> SEQUENCE: 2

Cys Gly Gly Val Lys Gly Asp Lys Gly Asn Pro Gly Trp Pro Gly Ala
1               5                   10                  15

Pro Gly

<210> SEQ ID NO 3
<211> LENGTH: 9
<212> TYPE: PRT
<213> ORGANISM: Artificial Sequence
<220> FEATURE:
<223> OTHER INFORMATION: Collagen IV peptide

```
<400> SEQUENCE: 3

Cys Gly Gly Gly Phe Pro Gly Glu Arg
1               5

<210> SEQ ID NO 4
<211> LENGTH: 15
<212> TYPE: PRT
<213> ORGANISM: Artificial Sequence
<220> FEATURE:
<223> OTHER INFORMATION: Laminin Peptide

<400> SEQUENCE: 4

Cys Gly Gly Ala Gly Gln Trp His Arg Val Ser Val Arg Trp Gly
1               5                   10                  15

<210> SEQ ID NO 5
<211> LENGTH: 9
<212> TYPE: PRT
<213> ORGANISM: Artificial Sequence
<220> FEATURE:
<223> OTHER INFORMATION: Collagen IV peptide

<400> SEQUENCE: 5

Cys Gly Gly Gly Ala Pro Gly Glu Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Collagen IV peptide
<220> FEATURE:
<221> NAME/KEY: MISC_FEATURE
<222> LOCATION: (3)..(3)
<223> OTHER INFORMATION: X is hydroxyproline

<400> SEQUENCE: 6

Gly Phe Xaa Gly Glu Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Collagen IV peptide
<220> FEATURE:
<221> NAME/KEY: MISC_FEATURE
<222> LOCATION: (3)..(3)
<223> OTHER INFORMATION: X is hydroxyproline

<400> SEQUENCE: 7

Gly Ala Xaa Gly Glu Arg
1               5

<210> SEQ ID NO 8
<211> LENGTH: 12
<212> TYPE: PRT
<213> ORGANISM: Artificial Sequence
<220> FEATURE:
<223> OTHER INFORMATION: Murine Laminin alpha-IV fragment

<400> SEQUENCE: 8

Ala Gly Gln Trp His Arg Val Ser Val Arg Trp Gly
1               5                   10
```

```
<210> SEQ ID NO 9
<211> LENGTH: 12
<212> TYPE: PRT
<213> ORGANISM: Artificial Sequence
<220> FEATURE:
<223> OTHER INFORMATION: Murine Laminin alpha-IV Fragment

<400> SEQUENCE: 9

Thr Trp Ser Gln Lys Ala Leu His His Arg Val Pro
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Peptide antagonists of TNF-alpha

<400> SEQUENCE: 10

Tyr Cys Trp Ser Gln Tyr Leu Cys Tyr
1               5

<210> SEQ ID NO 11
<211> LENGTH: 23
<212> TYPE: PRT
<213> ORGANISM: Artificial Sequence
<220> FEATURE:
<223> OTHER INFORMATION: Peptide antagonist of IFN-gamma
<220> FEATURE:
<221> NAME/KEY: MISC_FEATURE
<222> LOCATION: (4)..(4)
<223> OTHER INFORMATION: X is acetamidomethyl

<400> SEQUENCE: 11

Ala Tyr Cys Xaa Arg Asp Gly Lys Ile Gly Pro Pro Lys Leu Asp Ile
1               5                   10                  15

Arg Lys Glu Glu Lys Gln Ile
            20
```

SACCHARIDE-PEPTIDE HYDROGELS

CROSS REFERENCE TO RELATED APPLICATIONS

This application claims priority under 35 U.S.C. §119 from Provisional Application Serial No. 61/768,372 filed Feb. 22, 2013, the disclosure of which is incorporated herein by reference.

GOVERNMENT LICENSE RIGHTS

This invention was made with Government support under Grant No. EB006797, awarded by National Institutes of Health. The Government has certain rights in this invention.

TECHNICAL FIELD

The disclosure provides for biocompatible and biodegradable saccharide-peptide (SP) based hydrogels. The disclosure also provides for SP based hydrogels being functionalized with biological agents, such as biomimetic extracellular matrix (ECM) ligands and/or which can comprise encapsulated pharmaceutical agents and/or biochemical materials(s). The disclosure further provides for the use of the SP based hydrogels in treating a disease or disorder in a subject.

BACKGROUND

Cell therapy treatments have been developed using implantable polymer and polyethylene glycol based matrices. However, these matrices suffer from many drawbacks, including a lack of biocompatibility, minimal biodegradability, batch-to-batch variation, and limited tunability.

SUMMARY

The disclosure provides for innovative saccharide-peptide (SP) based hydrogels that exhibit a very favorable safety profile, are biocompatible, biodegradable, and can encapsulate a wide variety of biological materials and pharmaceutical agents. The disclosure additionally provides that the SP based hydrogels can be functionalized with a variety of biological agents, including but not limited to: peptides, proteins, antibodies, small molecule therapeutics, oligonucleotides, polynucleotides, imaging agents, carbohydrates, ligands, lipids, metals or metal containing complexes, or a combination of any of the foregoing. Moreover, the SP based hydrogels can further comprise one or more pharmaceutical agent(s) and/or one or more biological material(s), such as islets, that are encapsulated in the hydrogels.

The disclosure further provides for the use of the SP based hydrogels disclosed herein to controllably deliver a therapeutically effective agent to a subject, provide a matrix to implant cells in a subject, or can used to promote a biological effect in a subject.

In a particular embodiment, the disclosure provides for a hydrogel comprising one or more polymers which are comprised of a plurality of linked saccharide and peptide based monomers, and where the polymers can form one or more crosslinks under mild reaction conditions, wherein the hydrogel is biodegradable, and wherein the hydrogel is implantable in a subject at an extrahepatic site. In a further embodiment, the saccharide and/or peptide based monomers comprise either cysteine groups having the structure of:

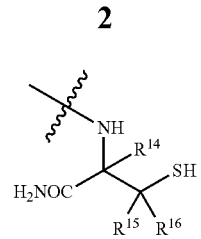

or vinyl sulfone groups having the structure of:

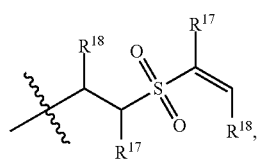

wherein $R^{14}$-$R^{18}$ are independently selected from the group consisting of H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cyclcoalkenyl, halide, alcohol, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, borinic ester; and wherein the one or more crosslinks are formed via cysteine-vinyl sulfone addition under suitable reaction conditions.

In another embodiment, the disclosure provides for a hydrogel wherein the saccharide and/or peptide based monomers comprise either cysteine groups having the structure of:

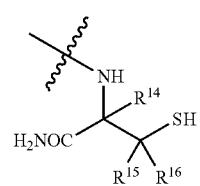

or vinyl sulfone groups having the structure of:

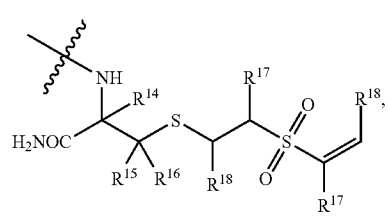

wherein $R^{14}$-$R^{18}$ are independently selected from the group consisting of H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cyclcoalkenyl, halide, alcohol, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, and borinic ester; and wherein the one or more crosslinks are formed via cysteine-vinyl sulfone addition under suitable reaction conditions.

In a certain embodiment, the disclosure provides for a hydrogel comprising: one or more polymers having a structure of Formula I, and one or more polymers having a structure of Formula II:

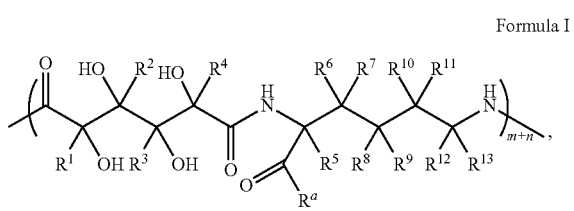

Formula I

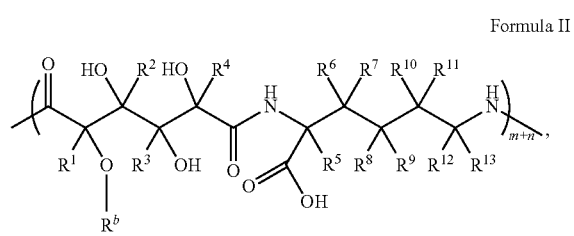

Formula II and
a plurality of cross links comprising the structure of Formula IV:

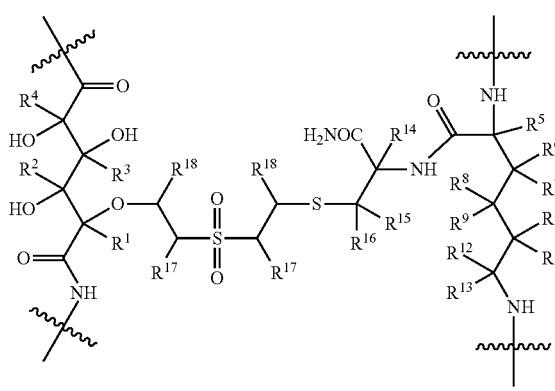

Formula IV wherein,
m and n are integers greater than one;
$R^a$ is independently an OH, or

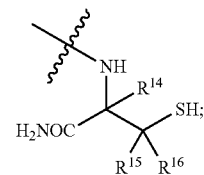

$R^b$ is independently a H or

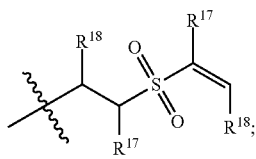

$R^1$-$R^{18}$ are independently selected from the group comprising H, optionally substituted $(C_{1-12})$-alkyl, optionally substituted $(C_{1-12})$-heteroalkyl, optionally substituted $(C_{1-12})$-alkenyl, optionally substituted $(C_{1-12})$-heteroalkenyl, optionally substituted $(C_{1-12})$-alkynyl, optionally substituted $(C_{1-12})$-heteroalkynyl, optionally substituted cycloalkyl, optionally substituted cyclcoalkenyl, halide, alcohol, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, borinic ester;

wherein if $R^1$-$R^{18}$ are H, then the hydrogel further comprises one or more pharmaceutical agents and/or one or more biological materials selected from islets, therapeutic natural products, DNA, RNA, proteins, carbohydrates, lipids, vitamins, pro-vitamins, or any combination thereof.

In another embodiment, the disclosure provides for a hydrogel comprising: one or more polymers having a structure of Formula I, and one or more polymers having a structure of Formula III:

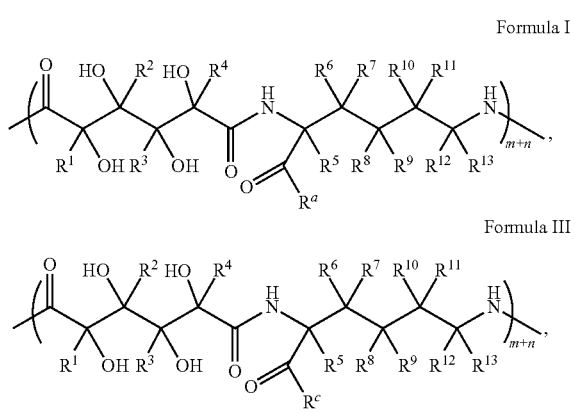

and
a plurality of cross links comprising the structure of Formula V:

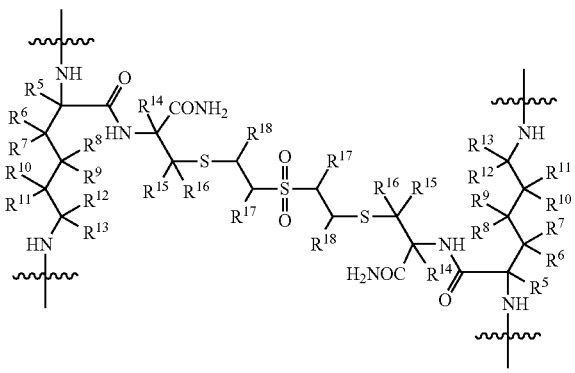

Formula V wherein,
m and n are integers greater than one;
$R^a$ is independently an OH, or

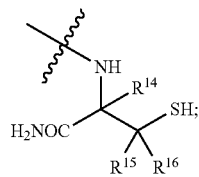

$R^c$ is independently a OH or

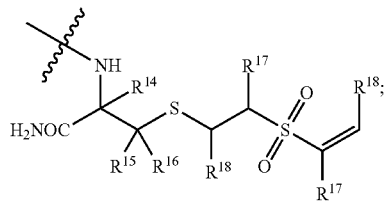

$R^1$-$R^{18}$ are independently selected from the group consisting of H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cyclcoalkenyl, halide, alcohol, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, and borinic ester.

In a further embodiment, the disclosure provides for a hydrogel disclosed herein is coupled or linked to one or more cell signaling ligands and/or cell signaling factors. Examples of cell signaling ligands and cell signaling factors include, but are not limited to, adhesion ligands, growth factors, chemokines, cytokines, receptor tyrosine kinase ligands, JAK-STAT ligands, transforming growth factor ligands, tumor necrosis factor ligands, antigens of the T-cell receptor, steroid receptor ligands, pancreatic and duodenal homeobox gene 1, soluble factors, G-protein-coupled receptor ligands, and neurotransmitters. In yet a further embodiment, the one or more cell signaling ligands and/or the one or more cell signaling factors are islet recognition motifs derived from laminin-α5 chain (Lm-α5) and collagen IV (Col IV). Specific examples of islet recognition motifs, include peptides which comprise the sequence of SEQ ID NO:1, SEQ ID NO:2, SEQ ID NO:3, SEQ ID NO:4, or SEQ ID NO:5.

In a certain embodiment, the disclosure provides for a hydrogel disclosed herein which further comprises one or more biological materials and/or one or more pharmaceutical agents. In a further embodiment, a hydrogel disclosed herein comprises one or more cells. In yet a further embodiment, a hydrogel disclosed herein comprises one or more cells encapsulated in the hydrogel in situ. In a particular embodiment, a hydrogel disclosed herein comprises encapsulated islets of human or non-human origin. In a further embodiment, the hydrogel further comprises encapsulated mesenchymal stem cells that over-express vascular endothelial growth factor.

In another embodiment, the disclosure provides a method of treating a disease or disorder in a subject comprising implanting a hydrogel disclosed herein a site in the subject, such as an extrahepatic site. In a further embodiment, implanting a hydrogel disclosed herein comprises in situ polymerization of the hydrogel, wherein one or more biological materials and/or one or more pharmaceutical agents are suspended in a solution comprising a polymer having a structure of Formula I and/or in a solution comprising a polymer having a structure of Formula II. In yet a further embodiment, islets are suspended in a solution comprising a polymer having a structure of Formula II. In another embodiment, the subject's disease or disorder can be treated by using cell therapy. In a preferred embodiment, a method for treating type 1 diabetes in a subject comprises implanting a hydrogel disclosed herein that contains encapsulated islets. In a further embodiment, islets that were implanted with a hydrogel disclosed herein secrete insulin into the blood stream in response to elevated blood glucose levels or hyperglycemia in the subject.

DESCRIPTION OF DRAWINGS

FIG. 1A-B provides a schematic of islet encapsulation in a saccharide-peptide (SP) based hydrogel of the disclosure. (A) Saccharide-peptide based polymers were generated through interfacial polymerization, which were then functionalized with either vinyl sulfone (VS) or cysteine (Cys). (B) Hydrogelation occurred by Michael addition in the presence of islets, when VS- and Cys-polymers were combined at an equimolar ratio.

FIG. 2A-E presents biocompatibility data of the SP based hydrogels disclosed herein as assessed in vitro. Peripheral blood mononuclear cells were incubated with phosphate buffered saline (PBS) (negative control), vicryl suture, SP based hydrogel, VS-polymer, Cys-polymer or Lipopolysaccharide (LPS) (positive control) and evaluated for cytokine gene activation after 18 hours: (A) interferon gamma (IFN-γ); (B) chemokine (C—X—C motif) ligand 1 (CXCL1); (C) granulocyte-macrophage colony-stimulating factor (GMCSF); (D) interleukin 6 (IL-6); and (E) tumor necrosis factor alpha (TNF-α). Gene activation in the presence of hydrogel and its constituents were not significantly different from PBS control. *(p<0.05). Mean±SEM, n=3.

FIG. 3A-B presents the effect of encapsulation on "Firefly" rat islet viability as evaluated by luminescence. (A) Luminescence signals from islets were monitored, and (B) quantified. Data are normalized by the luminescence measured on day 0. * indicates significantly different islet viability as compared to controls without hydrogel (p<0.05). Mean±SEM, n=3.

FIG. 4 presents the effects of hydrogel encapsulation on islet viability (live/dead) and function (DTZ). Islets were stained to detect live (green) and dead (red) cells, and also dithizone (DTZ) stained (red) to detect insulin granules on day 1, 14, and 28. Encapsulated islets were mostly alive and stained strongly for insulin granules by DTZ throughout, as compared to control islets.

DETAILED DESCRIPTION

Figure 5:
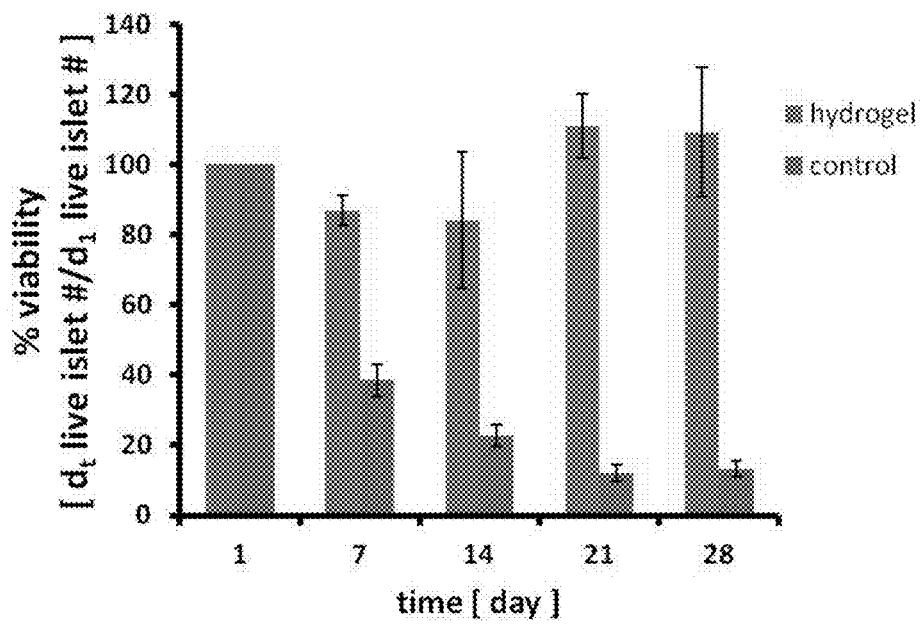
FIG. 5 demonstrates that the three dimensional structure of SP based hydrogel preserves islet viability in vitro. As shown, percentages of islets that were viable over time are considerably and significantly higher when encapsulated in SP based hydrogels than without encapsulation in SP based hydrogels.

As used herein and in the appended claims, the singular forms "a," "and," and "the" include plural referents unless the context clearly dictates otherwise. Thus, for example, reference to "an islet" includes a plurality of such islets and reference to "the biological material" includes reference to one or more biological materials or equivalents thereof known to those skilled in the art, and so forth.

Unless defined otherwise, all technical and scientific terms used herein have the same meaning as commonly understood by one of ordinary skill in the art to which this disclosure belongs. Although many methods and reagents similar to or equivalent to those described herein can be used in the practice of the disclosed methods and compositions, the exemplary methods and materials are now described.

All publications mentioned herein are incorporated herein by reference in their entirety for the purposes of describing and disclosing methodologies that might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in the publications that is similar to, or identical with, a term that has been expressly defined in this disclosure, the definition of the term as expressly provided in this disclosure will control in all respects.

As used herein, a "biological material" refers to any material that originates from or can be isolated from, a prokaryotic or eukaryotic organism (e.g., cell(s), DNA, RNA, proteins, carbohydrates, lipids, organic nutrients (i.e. vitamins and provitamins), and any combination made thereof). Specific examples of "biological materials" include, but are not limited to, differentiated mammalian cell(s) (e.g., Islets, dopamine producing cells, chondrocytes, and skeletal myoblasts), stem cells, collagen, elastin, keratin, therapeutic natural products (e.g., botulinum toxins, vincristine, irinotecan, etoposide and paclitaxel), and vitamins and provitamins (e.g., retinol, and panthenol). In a preferred embodiment, biological material(s) used with a hydrogel disclosed herein, refers to islets.

As used herein, a "pharmaceutical agent" refers to any chemical substance intended for use in the medical diagnosis, cure, treatment, or prevention of disease, disorder or condition.

As used herein, a "subject" refers to a vertebrate animal, preferably a mammal (e.g., human, dog, cat, horse, rat, mouse, rabbit, and primate).

As used herein, a "disease" or "disorder" refers to an impairment of the normal state or condition of a subject or one of the parts of the subject which interrupts or modifies the performance of its function, is typically manifested by distinguishing signs and symptoms, and is a response to environmental factors (e.g., malnutrition, industrial hazards, and climate), to specific infective agents (e.g., worms, bacteria, and viruses), to inherent defects of the organism (e.g., genetic anomalies), or to combinations of these factors. In a preferred embodiment, a disease or disorder disclosed herein is in reference to type 1 diabetes.

Diabetes is one of the most prevailing, costly, and debilitating diseases in the world. The prevalence of both Type 1 and Type 2 diabetes has increased in past decades and is expected to double in next 40 years. Type 1 diabetes (T1D) is an autoimmune disease characterized by the selective destruction of insulin-producing β cells in the pancreatic islets, leading to insulin deficiency and hyperglycemia. Treatment of T1D requires frequent blood glucose monitoring and insulin administration though subcutaneous injection or insulin pump. Poorly controlled blood glucose often leads fatal complications, such as renal failure, heart disease, and stroke. Alternatively, pancreas transplantation is performed mostly in patients who require kidney transplantation. While effective, the procedure is highly invasive and often associated with other complications. The donor pancreas used for this procedure must be of high quality; therefore, many sub-optimal pancreata cannot be used. Islet transplantation is currently being explored as an alternative approach to treat T1D patients who do not require a kidney transplant, but have frequent, uncontrollable hypoglycemic episodes. This minimally invasive procedure is associated with only minor complications and requires no hospitalization. Islet transplantation has been proven to be safe and effective by worldwide clinical trials during the past decade. Transplanted islets improve glycemic control, and more importantly, eradicate life-threatening hypoglycemic events.

Currently, islets are transplanted into the liver by infusing through the portal vein. Following transplantation, 80% of patients are free of insulin injections at one year. However, only 15% remain insulin independent after 5 years due to gradual graft dysfunction, indicating that the current procedure is far from optimal. A major problem is that as many as 60% of the injected islets are lost shortly after transplantation through inflammation but not allograft rejection. This acute islet loss appears to be a unique problem in the liver site, largely due to the instant blood mediated inflammation reaction (BMIR), innate immune reactions, as well as by the unique immune system of the liver consisting of liver natural killer cells and higher number of natural killer T cells. Even though the islets survive the initial insult, engrafted islets are continuously exposed to the liver environment which is different from the native pancreas, especially in terms of lower oxygen level, higher glucose concentration, and higher levels of toxins. Transplantation of islets outside of the liver is expected to improve islet engraftment and survival. Prevention of early stage islet loss will result in an increase of engrafted islets and consequently reduce the number of donor organs needed to treat a patient. Ultimately, development of appropriate extrahepatic islet transplantation would permit reversal of diabetes with a one to one donor/recipient ratio.

Donor islets are expected to function better and survive longer if they are transplanted to a site where the environment is similar to the pancreas. The new site must offer a large area to accommodate approximately 10 mL of donor cells and easy access for transplantation, examination, and removal. The pouch made by the omentum and intestinal wall are expected to be favorable sites for extrahepatic transplantation, since they preserve the physiological insulin delivery route. However, this procedure entails undesirable laparoscopic surgery. Islet transplantation into other sites, such as muscle, epidermal fat, space beneath the renal capsule, bone marrow, and subcutaneous site has been attempted in animal models, but not all sites are suitable for transplantation of a large islet volume. The subcutaneous site is attractive by offering large areas and easy accessibility, but due to few vasculatures lacks vascularization. Accordingly, a richly vascularized graft bed has to be prepared prior to islet implantation. Another hurdle in extrahepatic islet transplantation is the formation of large islet aggregates and subsequent islet necrosis.

Encapsulation of islets with biomaterials presents tremendous potential benefitting islet transplantation to an extrahepatic site. In pancreas, islets occupy only 1-2% of the total tissue mass and each islet is surrounded by native extracellular matrix (ECM). In addition to maintaining islet structure, ECM provides important signaling interactions to regulate multiple aspects of islet physiology, including survival, proliferation, and insulin secretion. During the process of islet isolation, however, a majority of the ECM components are destroyed due to the use of collagenase digestion. The disruption of ECMs leads to islet damage and fragmentation, accelerates cell clumping, and contributes to a significant reduction of islet viability and function during and after transplantation. Encapsulation of islets in a biomimetic scaffold should prevent islet disintegration and aggregation, facilitate islet distribution, and enhance islets survival and function in an extrahepatic site. In addition, semi-permeable polymer scaffolds can protect the encapsulated islets from direct contact with immune cells, while still allowing small molecules and proteins to diffuse through. To explore this approach, several types of biomaterials for islet encapsulation have been proposed. Biopolymers extracted from natural sources, such as collagen, fibronectin, heparin, and polysaccharides, often suffer from the lack of tunability, batch-to-batch variations and potential pathogen contamination and immunogenicity. A number of synthetic polymers have been used as scaffolds for islet encapsulation. Among them, poly(lactic acid) (PLA)

and poly(lactic-co-glycolic acid) (PLGA) are rigid hydrophobic polymers that require pre-fabricated scaffolds, coating with native ECM proteins, and relatively invasive surgical procedures for transplantation. Use of poly(vinyl alcohol) (PVA) for islet encapsulation requires freezing to form the scaffold, a process that results in islet loss and dysfunction. Compared to other synthetic biomaterials, hydrogels can closely mimic the hydrophilic content of native ECM, and can deliver cells in a minimally invasive manner. Among hydrogel scaffolds, polyethylene glycol (PEG)-based hydrogels have been investigated extensively for in vitro islet encapsulation. Despite many positive attributes, PEG hydrogels have several limitations including: (1) poor cell viability if the PEG-based hydrogels lack cell adhesion ligands; (2) the versatility for modifying the PEG-backbone is minimal due to the limited functionality of the PEG-backbone; and (3) the PEG-backbone is non-degradable, generating concerns for accumulation of PEG in vivo. PEG gels alone are not optimal for maintaining long-term islet function in vivo. The design of new scaffolds for clinically relevant islet transplantation is of utmost importance to support extrahepatic transplantation.

Although encapsulation of islets by hydrogels is very promising for islet transplantation to extrahepatic sites, short-term insults to islets (within the first two weeks after transplantation) likely impede long-term islet function. Major challenges faced by islets immediately after transplantation include the following: (1) non-ideal islet cell-matrix interactions causing cell death (e.g., stripped of ECMs, islets would die due to the lack of adequate signal transmitted through integrins); (2) inadequate protection from local inflammatory reactions caused by transplantation (e.g., diffusive cytokines can induce islet damage and apoptosis); and (3) insufficient vascularization leading to hypoxia. Since islets are richly vascularized in the body, a decrease in the oxygen level leads to substantial islet death.

The disclosure provides for innovative saccharide-peptide (SP) based hydrogels. The SP based hydrogels disclosed herein are comprised of natural building blocks (amino acids and saccharides) and have many useful properties including, but not limited to, fully biodegradable, non-clump forming, nontoxic, inexpensive to produce, versatile and highly functional. The synthesis of the SP based hydrogels is very simple and efficient. The saccharide monomer not only provides efficient linkage between the peptide units, but also improves the solubility and biocompatibility of the resulting polymers. Since the SP based hydrogels are composed of natural building blocks, the hydrogels will eventually degrade into natural, nontoxic, and bioabsorbable metabolites. The SP based hydrogels disclosed herein form under very mild conditions by simply mixing two SP polymers in culture medium. Accordingly, the SP based hydrogels are ideally suited for encapsulating biological materials, such as cells, and enabling injectable transplantation. The versatility and rich functionalities of the SP based hydrogels allow for convenient functionalization thereby greatly expanding the utility and optimization of the hydrogels as controlled drug delivery devices, for tissue engineering, and for transplantation of biological materials.

Equilibrium swelling data indicate the SP based hydrogels disclosed herein are highly swollen, having >95 wt % of water. The hydrogels are fully biodegradable and the degradation profile can be tuned by crosslinking density. For example, the density of the peptide ligands in both main chain and side chain functionalization can be varied from 0.05 to 5 mM, from 0.1 to 4 mM, from 0.5 to 3 mM, or from 1 to 2 mM. In a particular embodiment, the density of the peptide ligands in both main chain and side chain functionalization is about 0.05 mM, about 0.1 mM, about 0.15 mM, about 0.5 mM, about 0.75 mM, about 0.2 mM, about 0.3 mM, about 0.4 mM, about 0.5 mM, about 0.6 mM, about 0.8 mM, about 1.0 mM, about 1.5 mM, about 2.0 mM, about 2.5. mM, about 3 mM, about 3.5 mM, about 4.0 mM, about 4.5 mM, or about 5.0 mM. The microstructure of the hydrogels was investigated by Environment Scanning Electron Microscopy, indicating porous structure of the hydrated gels with porosity in the order of a few microns. Diffusion study of fluorescence-labeled dextrans (6 kDa-FITC and 30 kDa-TRITC dextrans) indicates that macromolecules can efficiently diffuse within the hydrogels, further confirming the porous structure. The mechanical stiffness (storage modulus) of the hydrogels can be controlled by the ratio of Cys/VS and/or pH for gelation. For example, in a certain embodiment, the ratio of CYS to VS polymers is 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, 1.5:1 to 1:1.5, or about 1:1. In another embodiment, the pH for gelation is about pH 4.5, about pH 5, about pH 5.5, about pH 6, about pH 6.5, about pH 7, about pH 7.5, about pH 8, or about pH 8.5. Finally, the cytotoxicity of the individual polymer components, i.e., Cys- and VS-functionalized polymers, were evaluated for a number of cell lines including PC-12, fibroblast, smooth muscle cells (SMCs), and MSCs by MTT assay. In all cases, the polymers show minimal cytotoxicity. These cells were encapsulated in 3D SP based hydrogels and the cells maintained very high viability in 3D environment for an extended period of time.

The SP-based hydrogels of the disclosure can be used as delivery devices by enabling the implantation of one or more biological materials and/or pharmaceutical agents into a limited area in a subject. Further, the hydrogels disclosed herein can also be used in tissue engineering and to generate two- and three-dimensional cell cultures.

In a particular embodiment, the disclosure provides for saccharide-peptide (SP) based hydrogels comprised of two alternately substituted saccharide-peptide based polymers that can form one or more crosslinks by Michael addition. In a further embodiment, a SP based hydrogel disclosed herein can further comprise one or more biological and/or one or more pharmaceutical agents in a liquid for in situ gelation of the hydrogel. In a particular embodiment, a hydrogel of the disclosure can be used to extrahepatically implant islets in a subject.

In a certain embodiment, the disclosure provides for a hydrogel comprised of natural building blocks, such as an amino acid and a saccharide (e.g., see FIG. 1), making both the hydrogel and its degradation products non-toxic and minimally immunogenic (e.g., see FIG. 2). In a further embodiment, a SP based hydrogel of the disclosure is comprised of one or more polymers which comprise a plurality of linked saccharide and peptide based monomers, where the polymers can form one or more crosslinks under mild reaction conditions such as using Michael addition, oxidative coupling, enzyme mediated cross-linking, esterification, or imine formation. Saccharides or sugars that can be used to make the hydrogels disclosed herein, include, but are not limited to, optionally substituted $C_4$-$C_8$ saccharides (e.g., glucose, allose, altrose, gulose, iodose, mannose, talose, and galactose). Examples of peptides that can be used to make the hydrogels disclosed herein include, but are not limited to, naturally occurring amino acids, and non-naturally occurring amino acids. In a further embodiment, the saccharide and/or peptide based monomers comprise either cysteine groups having the structure of:

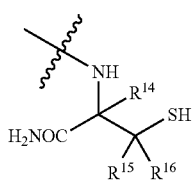

or vinyl sulfone groups having the structure of:

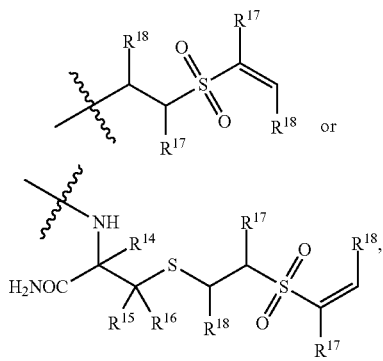

wherein $R^{14}$-$R^{18}$ are defined as in Formula I-III disclosed herein; and wherein the one or more crosslinks are formed via cysteine-vinyl sulfone addition under suitable reaction conditions.

Schemes I-IV provide for the synthesis of the SP based hydrogels disclosed herein. Schemes I-IV present exemplary methods to first synthesize alternately substituted saccharide-peptide polymeric components, that can be further cross-linked together to form a hydrogel of the disclosure. It should be understood, however, that obvious modifications can be made to the following schemes, such as performing steps in the presence of catalysts; use of alternative solvents/solvent systems, bases, and acids; substitution of reactants (e.g., Compound 5 although indicated herein as a substituted cysteine, could alternatively be any suitably substituted amino acid, including, but not limited to, serine, lysine, threonine, selenocysteine, and tyrosine); performing the reaction steps at elevated temperatures; and incorporating purification steps (e.g., extractions, dialysis, recrystallizations, and column chromatography). Accordingly, the following Schemes are presented as a general guide to synthesize hydrogels of the disclosure and it can be further expected that one of ordinary skill in the art can make obvious substitutions to one or more reaction steps presented in Scheme I, Scheme II, Scheme III, and/or Scheme IV.

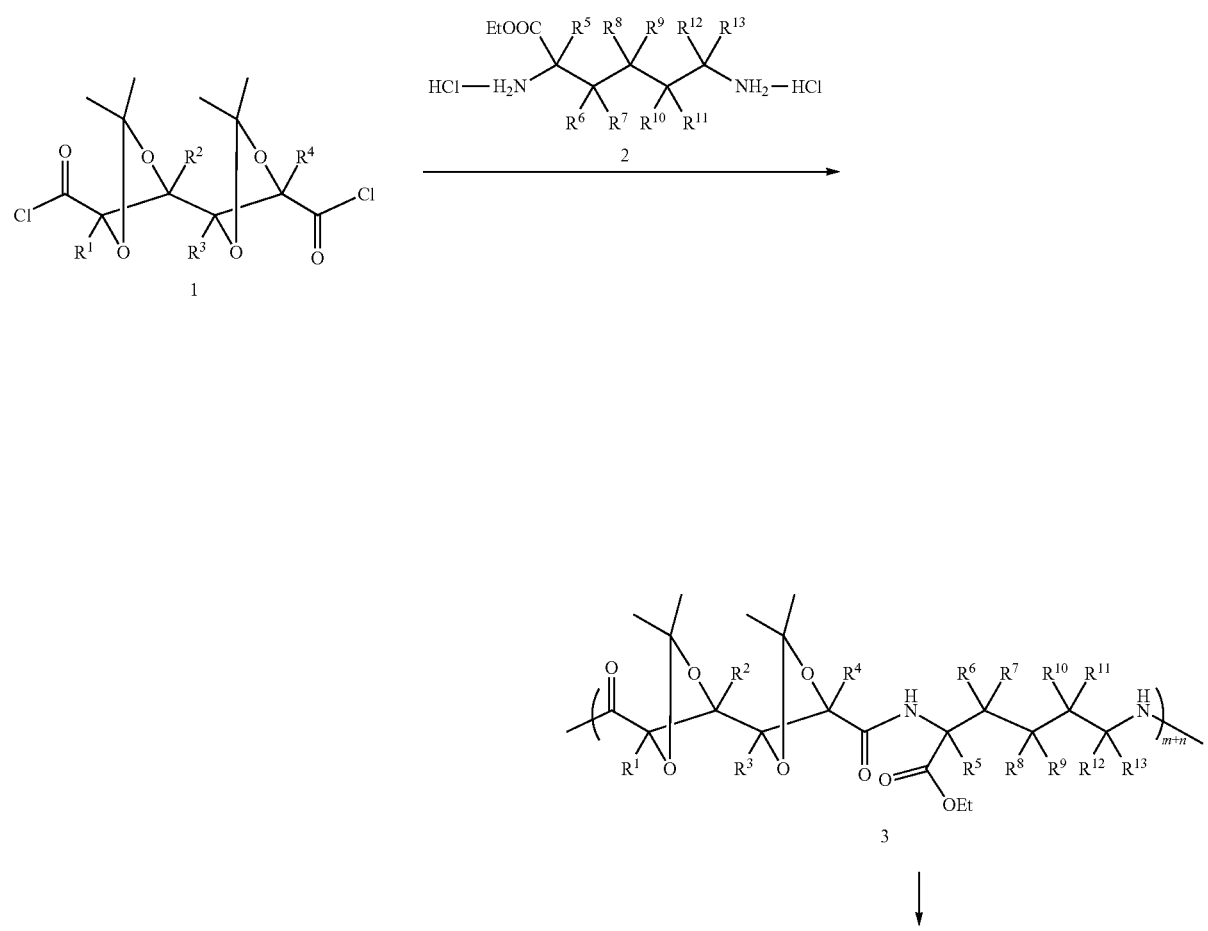

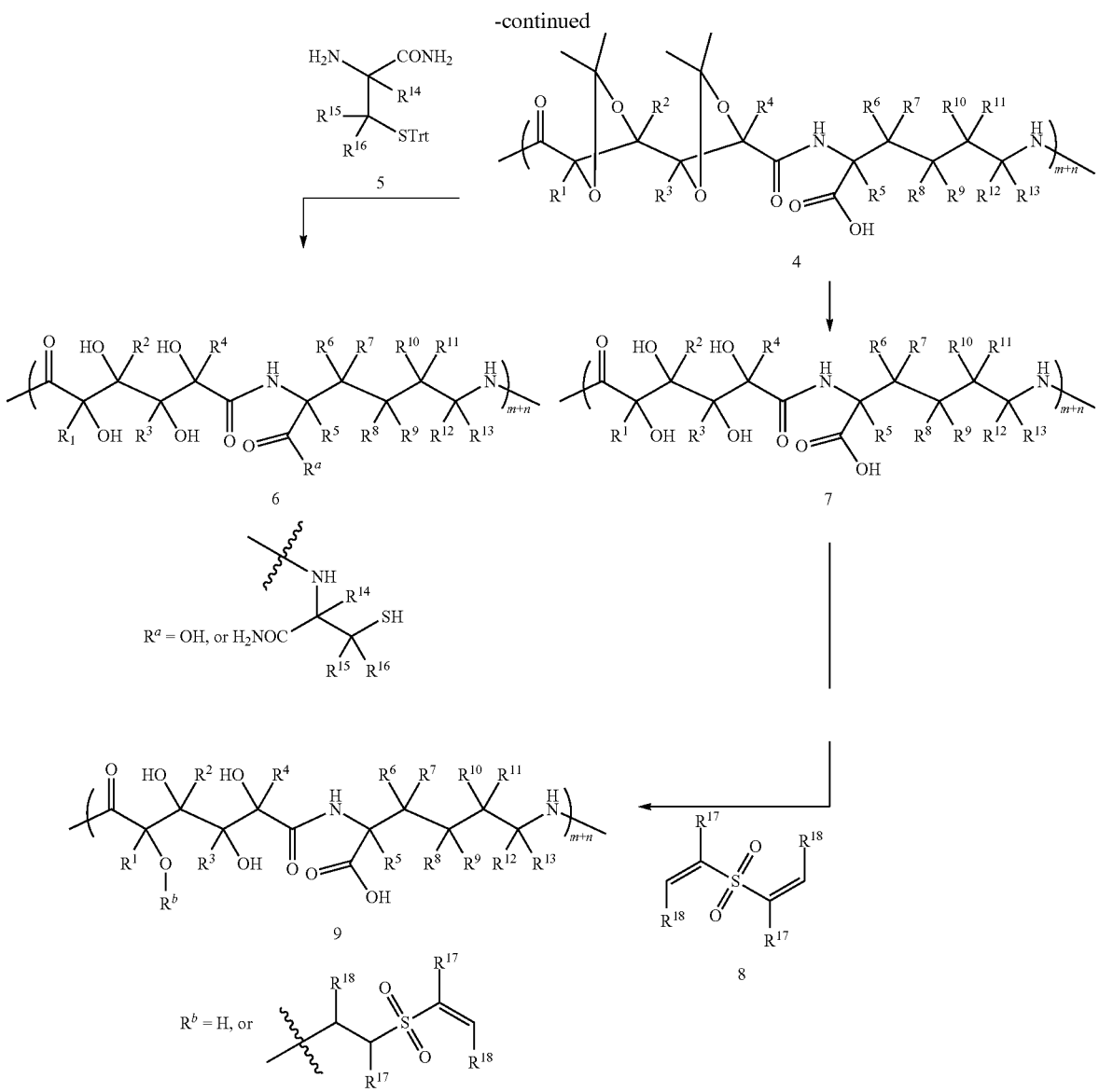

Compound 1 is reacted with compound 2 in the presence of an appropriate base, such as sodium carbonate, in a suitable solvent system, such as a combination chloroform and water, to give compound 3. Compound 3 is treated with an appropriate base, such as lithium hydroxide, to afford compound 4. Compound 4 is first coupled to compound 5 in the presence of suitable peptide coupling agent, such as HCTU, in the presence of a suitable base, such as DIPEA, to give a peptide coupled cyclic acetal intermediate that is then treated with an appropriate acid, such as trifluoroacetic acid, in a suitable solvent system, such as water, to give amino acid polymer 6. Alternatively, compound 3 is treated with an appropriate acid, such as trifluoroacetic acid, in a suitable solvent system, such as water, to afford compound 7. Compound 7 is reacted with compound 8 in the presence of an appropriate base, such as sodium hydroxide, to give a vinyl sulfone polymer 9.

Moreover, it should further be understood that any number of saccharides/sugars can be substituted for compound 1, and any number of peptide/amino acids can be substituted for compound 2 in Scheme I above. Moreover, many saccharides and peptides are readily available for purchase from vendors, such as Sigma-Aldrich, which can be further modified using common organic chemistry. For example, reactive side groups of a saccharide/sugar, such as hydroxyls, can be protected with suitable protecting group(s); hydroxyls and/or aldehydes can be oxidized to carboxylic acids (i.e., form aldaric acids); and/or carboxyl groups can be activated (e.g., form acyl halides). With such substitutions and modifications, the reaction conditions presented in Scheme I can in large part be utilized "as is" or with obvious modifications made thereof. In addition, procedures and teachings provided in the following references, which are incorporated herein in their entirety, can also be used to enable the production of the hydrogels of the disclosure: Chawla et al., *Biomacromolecules* (2011) 12:560-567; Chawla et al., *Biomaterials* (2012) 33:6052-6060; Liao et al., *Am Chem Soc.* (2009) 131:17638-46; Metzke et al., *J. Am. Chem. Soc.* (2003) 125:7760-7761; Urakami et al., *Biomacromolecules* (2008), 9:592-597; Metzke et al., *Biomacromolecules* (2008), 9:208-215; Metzke et al., *Angew. Chem., Int. Ed.* (2005), 44:6529-6533; and any reference cited therein.

In an alternate embodiment, the vinyl sulfone polymer can be made by using Scheme II:
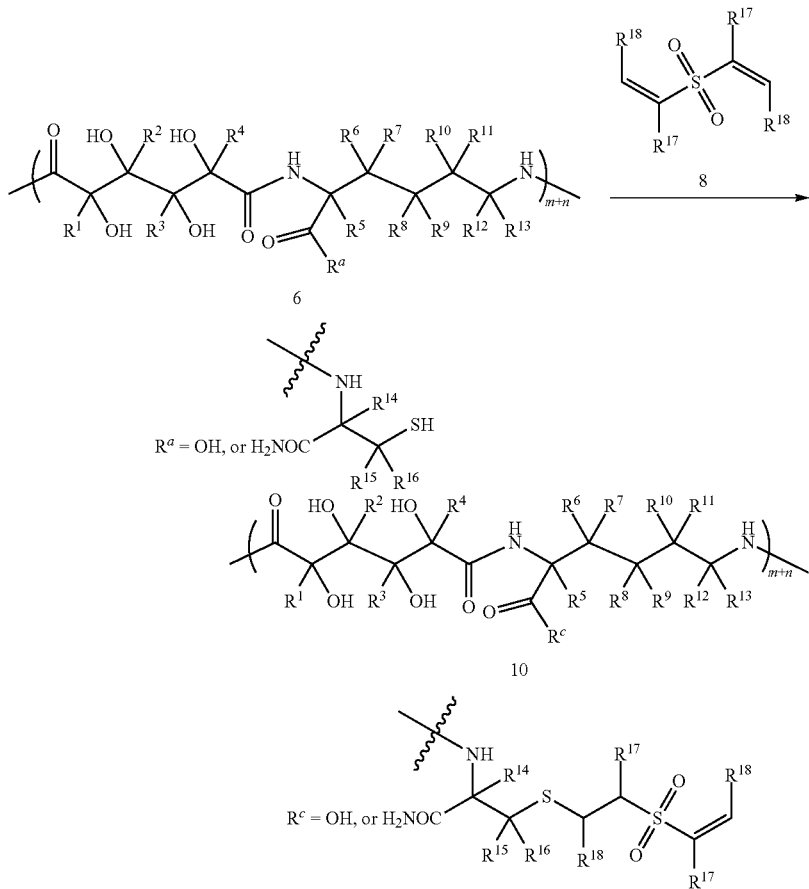
Compound 6 is reacted with excess of compound 8 in a suitable solvent system, such as phosphate buffer saline (pH 6.0), to afford a vinyl sulfone polymer 10.
A SP based hydrogel of the disclosure can then be made by cross-linking amino acid polymer 6 with vinyl sulfone polymer 9 as in Scheme III:
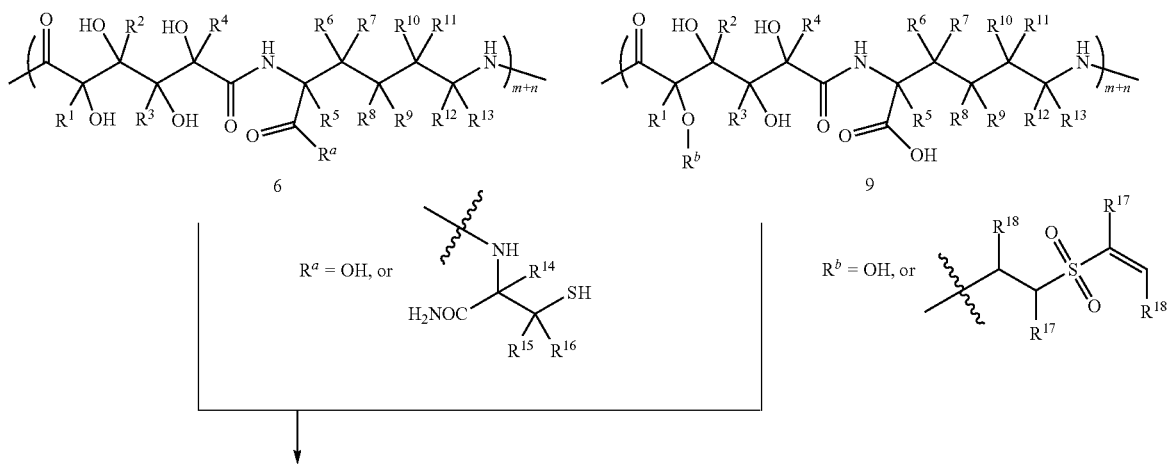

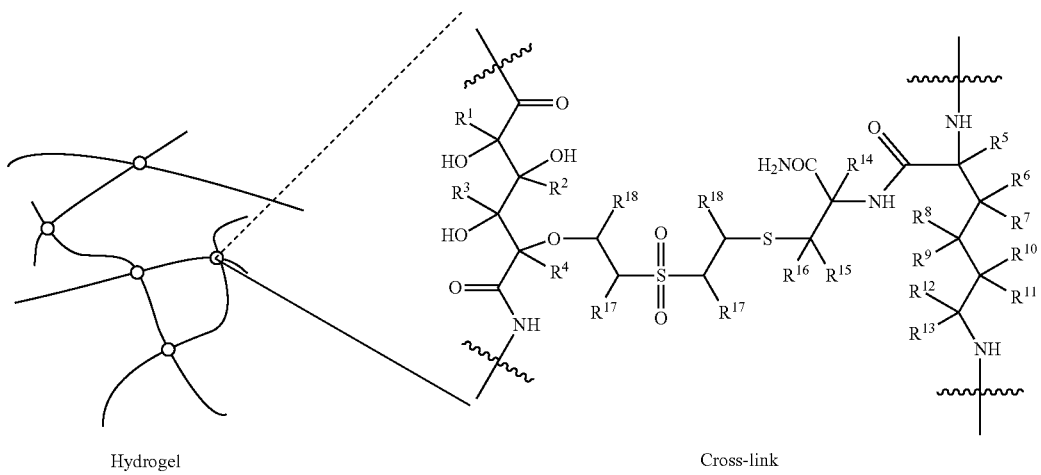

Hydrogel        Cross-link

Compound 6 and compound 9 are cross-linked together through a Michael type addition reaction in an appropriate buffer solution, which may or may not further comprise one or more biological materials, to afford a hydrogel of the disclosure.

An alternate SP based hydrogel of the disclosure can be made by cross-linking amino acid polymer 6 with vinyl sulfone polymer 10 as in Scheme IV:

Scheme IV

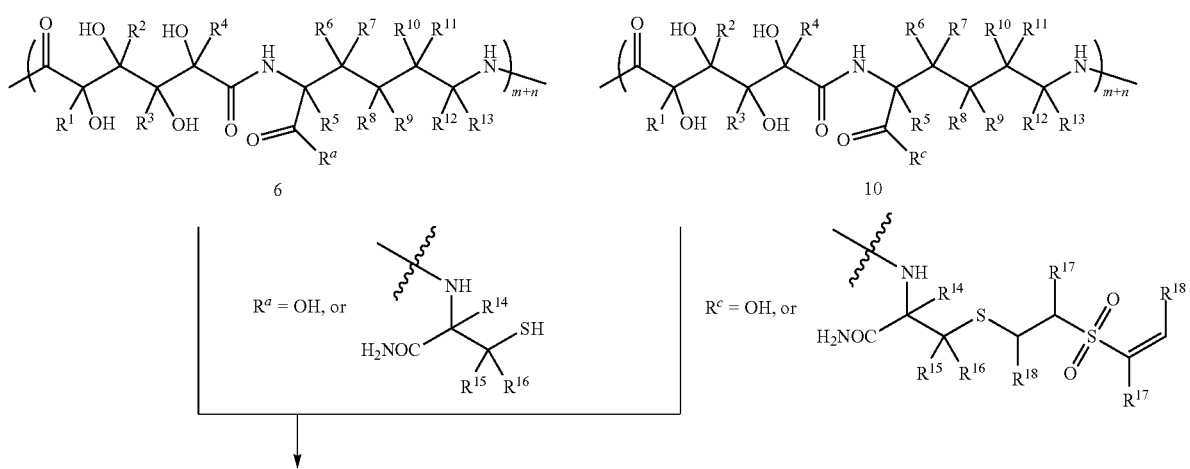

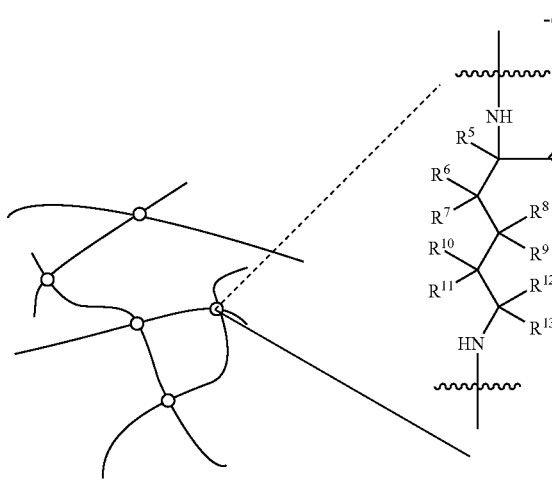

Hydrogel

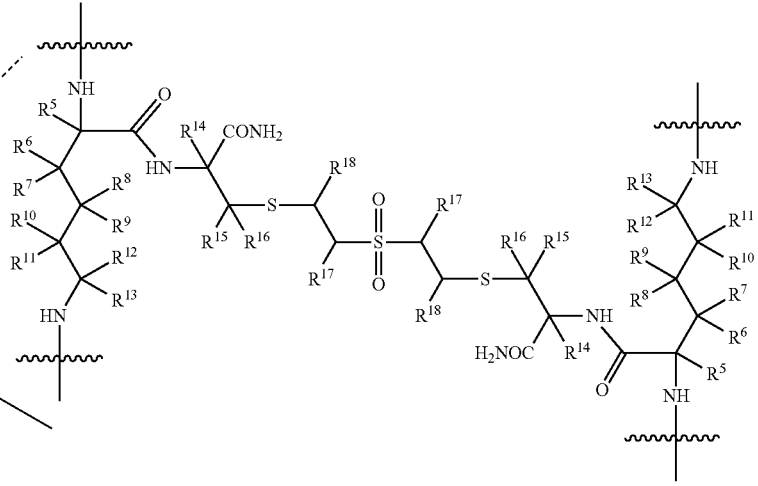

Cross-link

Compound 6 and compound 10 are cross-linked together through a Michael type addition reaction in an appropriate buffer solution, which may or may not further comprise one or more biological materials, to afford a hydrogel of the disclosure.

In a particular embodiment, a SP based hydrogel of the disclosure is comprised of a cross-linked polymer having the structure of Formula I:

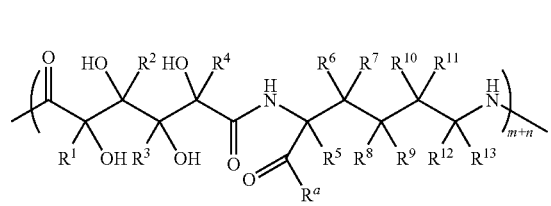

(I)

wherein, m and n are integers greater than one;

$R^a$ is independently an OH, or

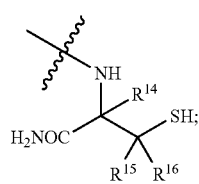

$R^1$-$R^{16}$ are independently selected from H, optionally substituted $(C_{1-12})$-alkyl, optionally substituted $(C_{1-12})$-heteroalkyl, optionally substituted $(C_{1-12})$-alkenyl, optionally substituted $(C_{1-12})$-heteroalkenyl, optionally substituted $(C_{1-12})$-alkynyl, optionally substituted $(C_{1-12})$-heteroalkynyl, optionally substituted cycloalkyl, optionally substituted cyclcoalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), and optionally substituted boron containing functional group (e.g., boronic acid, boronic ester, borinic acid, and borinic ester).

In another embodiment, a SP based hydrogel of the disclosure is comprised of a cross-linked polymer having the structure of Formula II:

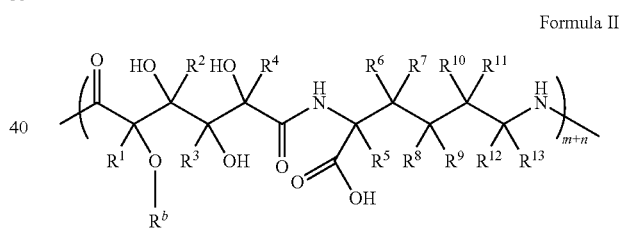

Formula II wherein, m and n are integers greater than one;

$R^b$ is independently a H or

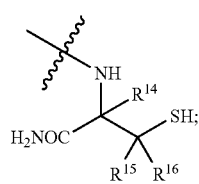

$R^1$-$R^{13}$ are defined as in Formula I; and $R^{17}$-$R^{18}$ are independently selected from H, optionally substituted $(C_{1-12})$-alkyl, optionally substituted $(C_{1-12})$-heteroalkyl, optionally substituted $(C_{1-12})$-alkenyl, optionally substituted $(C_{1-12})$-heteroalkenyl, optionally substituted $(C_{1-12})$-alkynyl, optionally substituted $(C_{1-12})$-heteroalkynyl, optionally substituted cycloalkyl, optionally substituted cyclcoalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), and optionally substituted boron containing functional group (e.g., boronic acid, boronic ester, borinic acid, and borinic ester).

In a particular embodiment, a SP based hydrogel of the disclosure is comprised of a cross-linked polymer having the structure of Formula III:

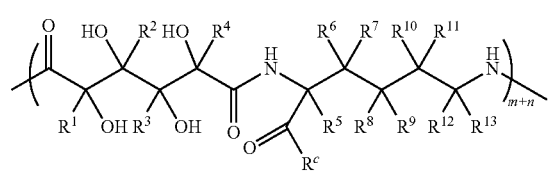

(III)

wherein, m and n are integers greater than one;

$R^c$ is independently an OH, or

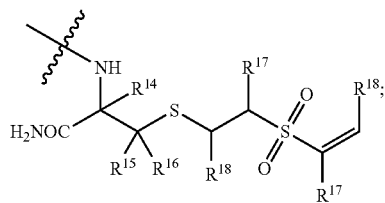

$R^1$-$R^{18}$ are independently selected from H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkenyl, optionally substituted ($C_{1-12}$)-alkynyl, optionally substituted ($C_{1-12}$)-heteroalkynyl, optionally substituted cycloalkyl, optionally substituted cyclcoalkenyl, halide, optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), and optionally substituted boron containing functional group (e.g., boronic acid, boronic ester, borinic acid, and borinic ester).

In a certain embodiment, a SP based hydrogel of the disclosure is comprised of one or more polymers having a structure of Formula I, one or more polymers having a structure of Formula II, and a plurality of crosslinks comprising the structure of Formula IV:

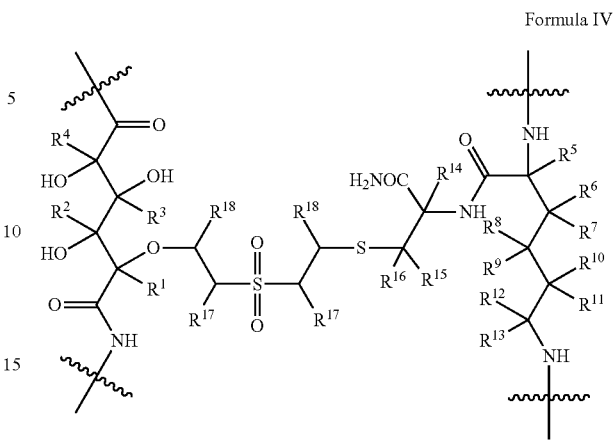

Formula IV wherein, $R^1$-$R^{18}$ are defined as in Formula I and Formula II disclosed herein. In a further embodiment, at least one of $R^1$-$R^{18}$ is not H. In another embodiment, when $R^1$-$R^{18}$ are H, then the hydrogel further comprises one or more biological materials and/or one or more pharmaceutical agents.

In an alternate embodiment, a SP based hydrogel of the disclosure is comprised of one or more polymers having a structure of Formula I, one or more polymers having a structure of Formula III, and a plurality of crosslinks comprising the structure of Formula V:

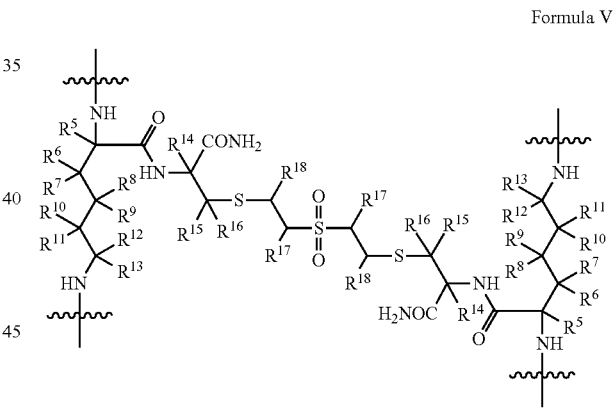

Formula V wherein, $R^1$-$R^{18}$ are defined as in Formula I and Formula III disclosed herein. In a further embodiment, at least one of $R^1$-$R^{18}$ is not H. In another embodiment, when $R^1$-$R^{18}$ are H, then the hydrogel further comprises one or more biological materials and/or one or more pharmaceutical agents.

Figure 6:
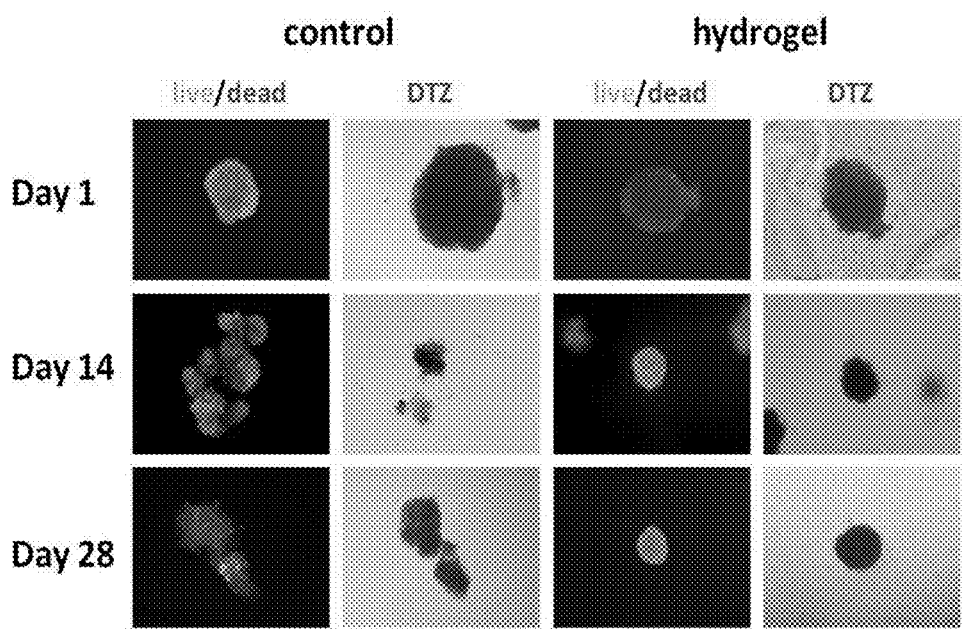
FIG. 6 presents a replicate experiment of the effects of hydrogel encapsulation on islet viability (live/dead) and function (DTZ). Islets were stained to detect live cells (green) using fluorescent diacetate and dead cells (red) using propidium iodide, and also DTZ stained (red) to detect insulin granules on day 1, 14, and 28. Encapsulated islets were mostly alive and stained strongly for insulin granules by DTZ throughout, as compared to control islets.
Figure 7:
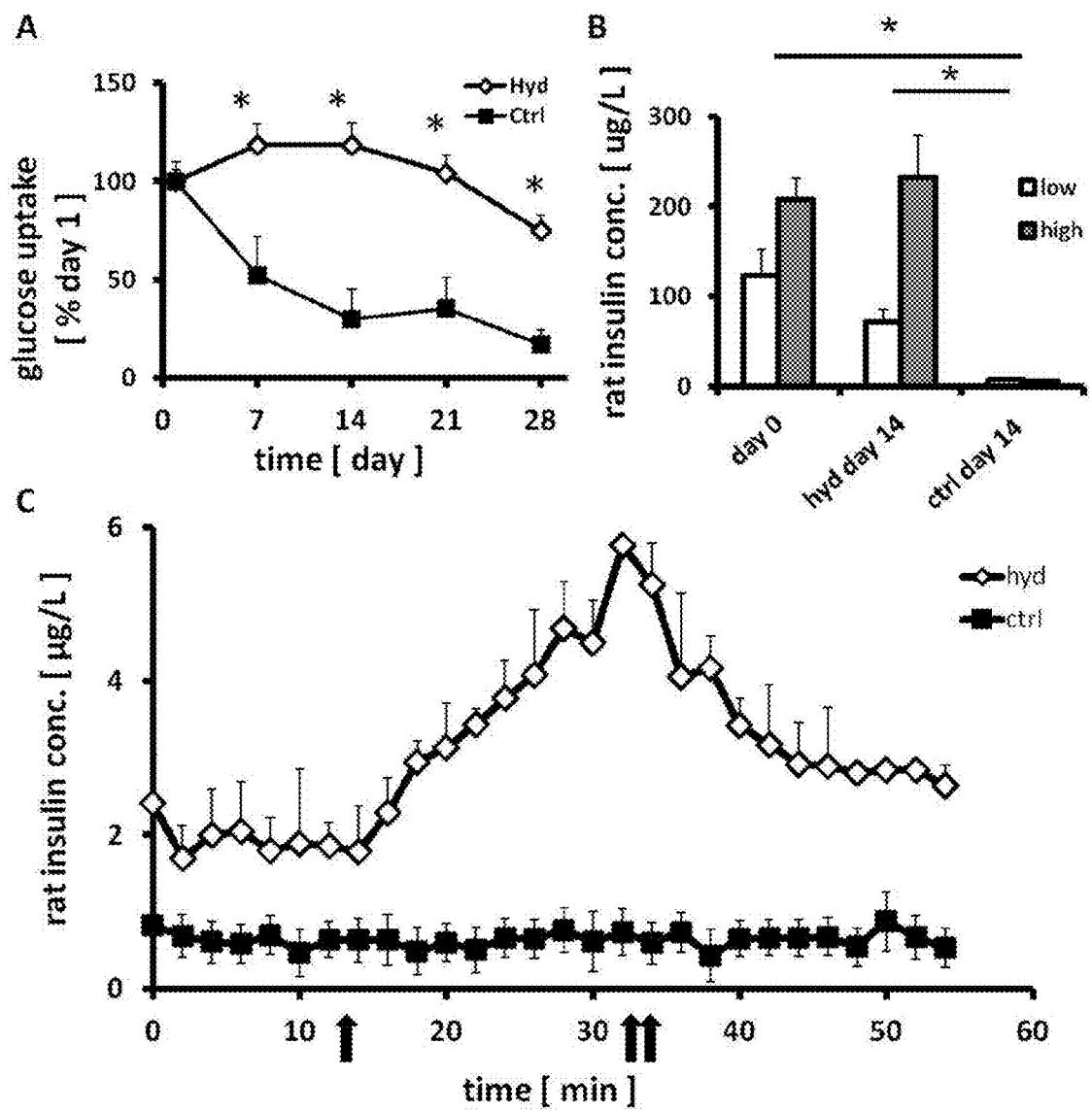
FIG. 7A-C presents in vivo data with respect to the maintenance of islet metabolism and function with a SP based hydrogel of the disclosure. Effects of encapsulation on (A) rat islet glucose consumption (n=3) and (B) insulin secretion in static incubation on day 14 (n=4). (C) On day 28, dynamic insulin release of islets were assessed by sequential stimulating by low- (3 mM), high- (17 mM, one arrow), and low- (3 mM, double arrow) glucose media using a perifusion system (n=3). * indicates significantly different to control islets (without hydrogel, p<0.05). Mean±SEM.

In a particular embodiment, due to its intrinsic biomimetic functionality, hydrogels disclosed herein have excellent in vivo biocompatibility (e.g., see FIG. 6A) and cytocompatibility for biological materials, such as islets (e.g., see FIG. 4). In another embodiment, hydrogels disclosed herein can be gelled using mild in situ cross-linking conditions thereby minimizing damage to biological materials and/or pharmaceutical agents during gelation. In yet another embodiment, hydrogels disclosed herein allow for the use of simple injection procedures to implant the hydrogels. Major surgery is therefore not necessary. In a further embodiment, biological materials encapsulated in a hydrogel disclosed herein are prevented from aggregating and undergoing necrosis (e.g., see FIG. 4). The disclosure further provides that hydrogels disclosed herein protect encapsulated biological materials from coming into direct contact with blood, preventing a blood mediated inflammation reaction (BMIR), and/or from coming into contact with immune cells, at least for the initial post-transplantation period, resulting in high viability and function for transplanted biological materials (e.g., see FIG. 6).

Signaling interactions between islet cells and ECM regulate multiple aspects of islet physiology, including survival, proliferation, and insulin secretion. During the process of islet isolation, however, a majority of the ECM components are destroyed due to the use of various enzymatic digestions, resulting in significant reduction of islet survival and function. Therefore, for islet encapsulation and transplantation, it is desirable to design a hydrogel that can recapitulate such islet-matrix interactions in order to prevent islets apoptosis and facilitate rapid re-establishment of natural ECMs. For this purpose, the disclosure provides for the functionalization of the SP based hydrogels disclosed herein with cell adhesion ligands (e.g., biomimetic ECM ligands) to promote islet-matrix interactions.

In a particular embodiment, a SP based hydrogel disclosed herein is linked to one or more cell signaling ligands and/or one or more cell signaling factors. Examples of cell signaling ligands and factors, include, but are not limited to, cell adhesion ligands, growth factors, chemokines, cytokines, receptor tyrosine kinase ligands, JAK-STAT ligands (e.g., interleukins), transforming growth factor ligands, tumor necrosis factor ligands, antigens of the T-cell receptor, steroid receptor ligands, pancreatic and duodenal homeobox gene 1, soluble factors, G-protein-coupled receptor ligands, and neurotransmitters. In a further embodiment, a SP based hydrogel disclosed herein is linked with cell adhesion ligands (e.g., biomimetic ligands) for promoting islet-matrix interactions and ECM recovery. Biomimetic islet cell adhesive peptide ligands derived from native ECM can be linked to the SP based hydrogel disclosed herein to recapitulate native islet-matrix interactions. The improved islet-hydrogel interactions should reduce islet apoptosis following transplantation and facilitate rapid re-establishment of native ECMs for islet long-term health and function. While the SP based hydrogel interferes with inflammatory cells infiltrating and coming in direct contact with the encapsulated islets, inflammatory cytokines can diffuse into the SP based hydrogel and trigger apoptosis of encapsulated islet cells. Accordingly, cytokine antagonists may be linked to the SP based hydrogel disclosed herein to prevent cytokine-triggered β cell apoptosis. Examples of cytokine antagonists include soluble cytokine receptors, cytokine peptides, cytokine antibodies, and cytokine-antagonizing peptides.

In another embodiment, a SP based hydrogel disclosed herein is linked with cell adhesion ligands (e.g., biomimetic ligands) for promoting cell-matrix interactions and ECM recovery. Examples of cell adhesion ligands include, but are not limited to, Ig superfamily (IgSF); addressins, such as CD34 and GLYCAM-1; integrins, such as collagen, fibrinogen, fibronectin, laminin, and vitronectin; cadherins; and selectins. In a particular embodiment, the disclosure provides for linking the SP based hydrogel (e.g., forming covalent bonds) with islet recognition motifs derived from laminin-α5 chain (Lm-α5) and collagen IV (Col IV). Col IV and laminin are the most abundant matrix proteins found in the vascular basement membrane (BM) identified within islets in situ. Although there are 15 isoforms for laminin, only Lm511 (α5β1γ1) is secreted by endocrine cells in the adult human pancreas and is found adjacent to islets. Lm511 is also found abundantly in the BM lining of the vasculatures in rat islets. Therefore, Lm-α5 and Col IV derived ligands could be expected to promote islet-hydrogel interactions by mimicking the native microenvironment.

In a specific embodiment, the SP based hydrogel disclosed herein is linked with cell adhesion ligands that are associated with islet cells, such as the adhesive ligands derived from laminin (e.g., laminin-α5) and collagen (e.g., collagen IV). In another embodiment, the SP based hydrogel disclosed herein is linked with islet cell adhesive peptides derived from Lm-α5 and Col IV that are known to bind to islet integrins. In yet a further embodiment, the islet cell adhesive peptides derived from Lm-α5 and Col IV have the peptide sequences presented in TABLE 1.

TABLE 1

Cell Adhesion Ligands

| Label | Cell Adhesion Ligand | Sequence |
|---|---|---|
| A11 | Laminin | IKVAV (SEQ ID NO: 1) |
| A13 | Collagen IV (Cell Binding) | CGGVKGDKGNPGWPGAPG (SEQ ID NO: 2) |
| A14 | Collagen IV (L1) | CGGGFPGER (SEQ ID NO: 3) |
| A16 | Laminin (Lm511, L3) | CGGAGQWHRVSVRWG (SEQ ID NO: 4) |
| A19 | Collagen IV (L2) | CGGGAPGER (SEQ ID NO: 5) |

In a further embodiment, hydrogels disclosed herein can be further functionalized with various signaling ligands and factors leading to possible significant enhancements in a biological material's function and viability and/or a pharmaceutical agent's effectiveness in vivo. Accordingly, it should be understood that for the SP based hydrogel disclosed herein, (e.g., the polymers made by Scheme I-IV), the polymers may be further functionalized by linking various biological agents (e.g., biomimetic ECM ligands and/or cytokine antagonists) to the backbone of the polymers and/or to the side chains of the polymer. The functionalization of the polymers may occur prior to polymerization step (e.g., functionalizing the starting materials) or after the polymerization step.

The disclosure also provides for hydrogels disclosed herein for use in vitro cultures to grow and maintain biological materials, such as islets cells. Moreover, hydrogels disclosed herein can further comprise biological materials and/or pharmaceutical agents for in vivo or in situ transplantation. In a particular embodiment, a hydrogel disclosed herein further comprises islets that allow for the stimulated production of insulin in vitro for extended time periods post islet isolation (e.g., greater than thirty days). In a further embodiment, hydrogels of the disclosure can be used to transplant islets to an extrahepatic site in a subject in order to lower the subject's blood glucose levels by releasing insulin. The transplanting of islets outside of the liver prevents post-transplant, acute donor islet destruction, thereby increasing the percentage of type 1 diabetes subjects achieving long-term insulin-independence. Accordingly, in a particular embodiment, hydrogels of the disclosure provide effective methods to treat subjects with type 1 diabetes by transplanting islets at extrahepatic sites.

In a further embodiment, a SP based hydrogel of the disclosure that is comprised of one or more polymers having a structure of Formula I, one or more polymers having a structure of Formula II, and a plurality of crosslinks comprising the structure of Formula IV, further comprises one or more biological materials and/or one or more pharmaceuticals agents, wherein the materials and/or agents may or may not be encapsulated in the hydrogel.

In another embodiment, an SP based hydrogel of the disclosure that is comprised of one or more polymers having a structure of Formula I, one or more polymers having a structure of Formula III, and a plurality of crosslinks comprising the structure of Formula V, further comprises one or more biological materials and/or one or more pharmaceuticals agents, wherein the materials and/or agents may or may not be encapsulated in the hydrogel.

In in vitro studies presented herein, the SP based hydrogel of disclosure and its individual polymer components induced minimal inflammatory cytokine activation in peripheral blood mononuclear cells (PBMC), implying that the degraded products from the hydrogel should cause a minimal immune response (e.g., see FIG. 2). In agreement with the in vitro results, the SP based hydrogel disclosed herein induced a very minimal inflammatory cell infiltration in vivo (e.g., see FIG. 6A). In order to prevent massive islet necrosis in extrahepatic islet placement, it is necessary to prevent clumping of the islets. The mild Michael type addition reaction permitted a suspension of isolated islets to be encapsulated in a hydrogel without clumping. After gelation was initiated, islets remain separated from each other and did not form any clumps. Islet necrosis was limited or not observed. In a particular embodiment, a SP based hydrogel of the disclosure is gelled from a solution comprising one or more polymers of Formula I and/or a solution comprising one or more polymers of Formula II, wherein the solution(s) further comprises one or more pharmaceutical agents and/or one or more biological materials, wherein the agents and/or materials are encapsulated in the resulting hydrogel when the solutions are mixed together. In a further embodiment, solutions comprising one or more polymers of Formula I further comprise suspended islets. In an alternate embodiment, solutions comprising one or more polymers of Formula II further comprise suspended islets. In a certain embodiment, a SP based hydrogel of the disclosure is gelled from a solution comprising one or more polymers of Formula I and/or a solution comprising one or more polymers of Formula III, wherein the solution(s) further comprises one or more pharmaceutical agents and/or one or more biological materials, wherein the agents and/or materials are encapsulated in the resulting hydrogel when the solutions are mixed together. In a further embodiment, solutions comprising one or more polymers of Formula I further comprise suspended islets. In an alternate embodiment, solutions comprising one or more polymers of Formula III further comprise suspended islets.

Utilization of a synthetic extra cellular matrix (ECM) scaffold, such as a SP based hydrogel disclosed herein, immobilizes islets at the site of injection, supports the 3D structure, and alleviates further islet damage. Histological examination of biopsied graft sites indicated that by the time a hydrogel of the disclosure started to degenerate, islets were already embedded in the surrounding tissues.

The SP based hydrogels disclosed herein exhibited several unique properties, such as biocompatibility, ease of handling, can be cross-linked in mild physiological conditions, and injectable for in situ polymerization for transplantation. Moreover, the hydrogels disclosed herein can be modified to provide instructional cues to control cell behavior, such as by linking one or more cell signaling ligands and/or one or more cell signaling factors to the SP based hydrogel.

It should be understood, that the SP based hydrogels of the disclosure can deliver a biological materials and/or pharmaceutical agents in a controlled manner (i.e. the rate in which the hydrogel biodegrades) to a defined location. Therefore, any disease or disorder that can be treated, ameliorated, or attenuated by the controlled release of a biological material and/or pharmaceutical agent from a defined location is treatable by a hydrogel of the disclosure. For example, diseases or disorders that can be treated by cell therapy (e.g., type 1 diabetes, Parkinson's disease, Alzheimer's disease, cancer, spinal cord injuries, heart damage, hematopathological conditions, baldness, deafness, blindness and vision impairment, amyotrophic lateral sclerosis, graft vs. host disease, and Crohn's disease) are particularly amendable to being treated by a hydrogel disclosed herein that further comprises an encapsulated cell(s) or multiple types of cell(s) (e.g., stem cells in combination with differentiated cells).

In a particular embodiment, the disclosure provides for a hydrogel disclosed herein which comprises encapsulated islets that can be transplanted in an extrahepatic location of a subject to treat type 1 diabetes. Examples of extrahepatic locations include, but are not limited to, omentum, subscutaneous sites, adipose tissue, and under the renal capsule. In an alternate embodiment, the disclosure provides for treating a subject with type 1 diabetes by injecting a hydrogel forming solution comprising a vinyl sulfone-polymer and suspended islets and a cysteine-polymer, wherein the islets are encapsulated by the hydrogel in situ.

In a further embodiment, in order to facilitate rapid angiogenesis, mesenchymal stem cells (MSCs) which over-express vascular endothelial growth factor (VEGF) can be co-encapsulated with islets in an SP based hydrogel disclosed herein.

The following examples are intended to illustrate but not limit the disclosure. While they are typical of those that might be used, other procedures known to those skilled in the art may alternatively be used.

EXAMPLES

The hydrogels disclosed herein were extensively tested in studies to evaluate the hydrogels' characteristics and to test the feasibility of using hydrogels comprising islets in treating diabetes. In particular, the studies demonstrated that the hydrogels of the disclosure were (1) biocompatible in vivo; (2) promoted viability of islets post-isolation; and (3) maintained islet insulin secretion function in response to high glucose in vitro and in vivo, which can easily be lost in isolated islets (e.g., see FIG. 1).

The results presented herein, further demonstrate the capability of the hydrogels of the disclosure in maintaining the viability of biological cells and their associated functions in vitro. A biological cell is supported and surrounded (encapsulated) by a hydrogel disclosed herein, resulting of promoting or maintaining the cell's viability and function in vitro and in vivo. For example, islets encapsulated by a hydrogel disclosed herein resulted in maintenance of islet function and viability for over 4 weeks (67% viability) until hydrogel degradation (e.g., FIG. 3B). By contrast, cells encapsulated by other methods did not achieve the exceptional results as the hydrogels disclosed herein. For example, the viability of polyethylene glycol (PEG)-encapsulated single beta cells, such as MIN-6 cells and RIN-m5F cells, was only 20% viability on day 10 when encapsulated without the addition of adhesion ligands; while the viability of alginate-encapsulated islets demonstrated 41% viability by day 12 without the presence of supporting sertoli cells. By using the hydrogels disclosed herein, stimulated insulin production in hydrogel-encapsulated islets was far superior to that of suspension cultured islets in both static incubation assays (day 14) and dynamic insulin release assays (day 28) (e.g., see FIG. 5). Compared to alternative hydrogels known in the art, the hydrogels disclosed herein exhibited properties that were so unexpectedly superior, that it is not necessary to provide adjuvants in order to maintain islets viability and activity. Notwithstanding the foregoing, the disclosure does provide in a particular embodiment that a hydrogel disclosed herein may be further functionalized with cell adhesion ligands or inclusion of supporting cells.

Considering that islets are highly sensitive cells that are more susceptible to functional impairment than beta cell lines, in vivo studies for insulin production were performed. Insulin responsiveness was evaluated in a rodent model for diabetes reversal using hydrogels of the disclosure which further comprised encapsulated islets. In order for rats to become normoglycemic, the transplanted islets have to survive, release insulin in response to glucose, and the released insulin has to enter into the blood circulation. In the studies, hydrogels comprising encapsulated islets were able to lower hyperglycemia in an extraheptic site, the omentum, in comparison to control islets (e.g., see FIG. 6D). The results demonstrate that hydrogels of the disclosure are not only novel and innovative materials but can also be used effectively to deliver encapsulated biological materials and/or pharmaceutical agents to treat a disease or disorder in a subject.

Experimental Animals. LEW rats were used as islet donors and transplant recipients. Islets were isolated as described in Ishiyama et al., *Transplantation* (2011) 91:952-960, which is incorporated herein in its entirety.

Preparation of Saccharide/Peptide Hydrogels. Saccharide/peptide (SP)-based hydrogels were prepared by following the (1) procedure described in Chawla et al., *Biomacromolecules* (2011) 12:560-567, which is incorporated herein in its entirety, and reproduced below as Scheme VI, or (2) by following the reactions presented in Scheme VII. Briefly, polymers were prepared by dissolving vinyl sulfone (VS)- and cysteine (Cys)-copolymers at a concentration of 65 mg/mL in Dulbecco's Modified Eagle's Medium (Gibco Life Technologies, Carlsbad, Calif.). Vinyl sulfone (VS)-polymer was added to cells and mixed. To which, was added Cys-polymer. A hydrogel was then formed within 10 minutes via a mild Michael type addition reaction.

Scheme VI

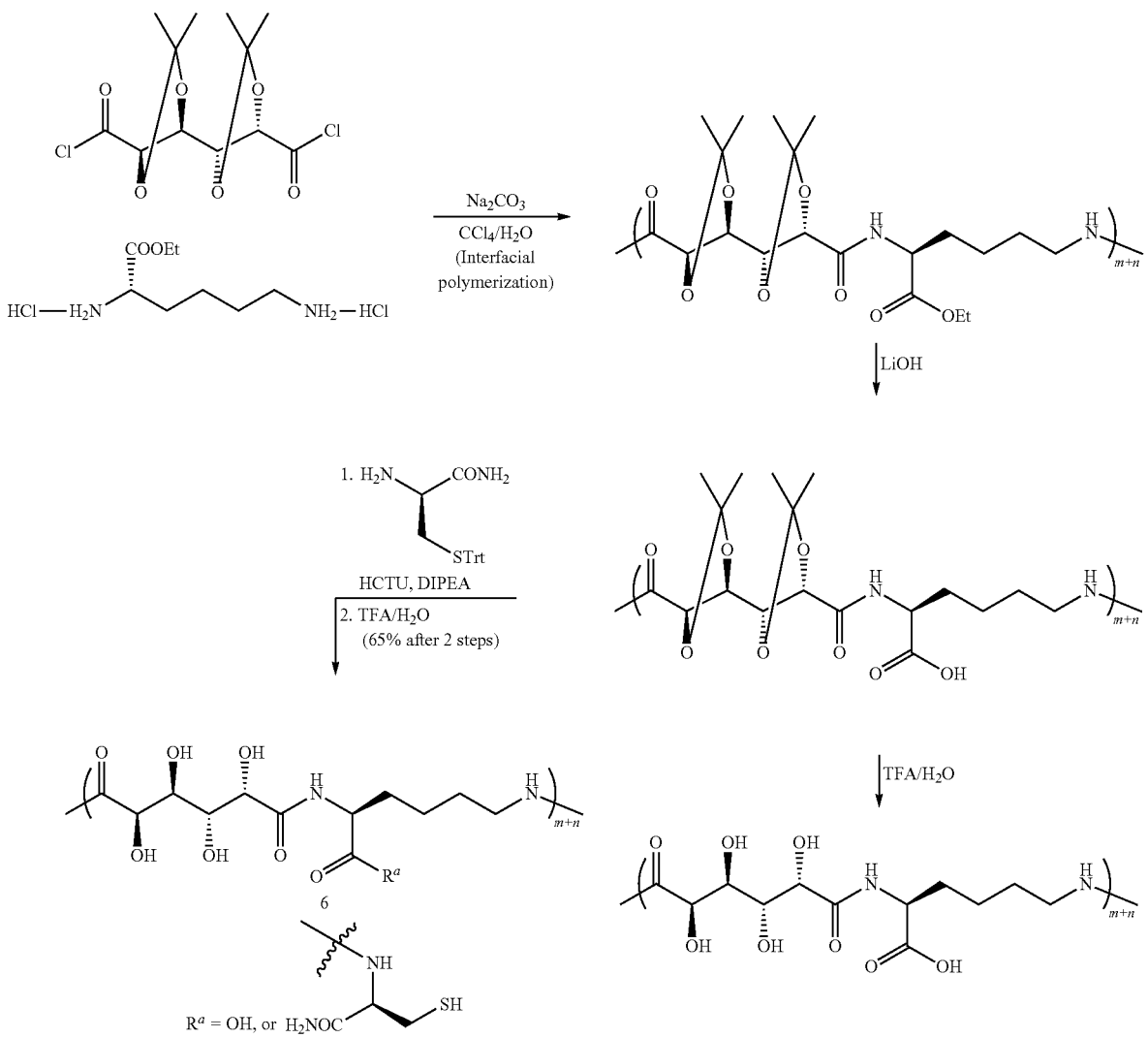

-continued
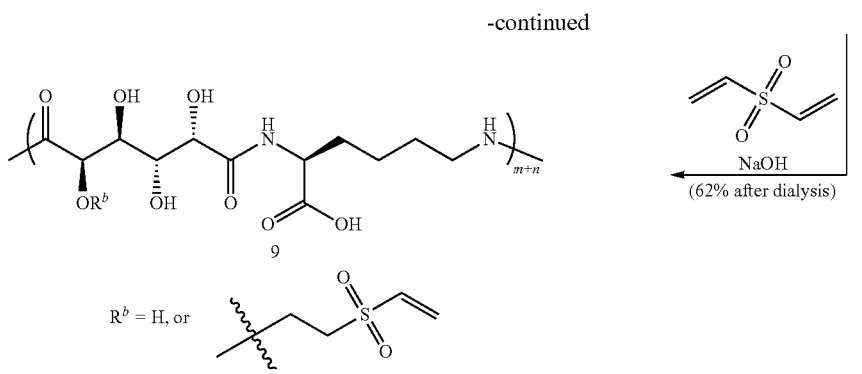
9
$R^b$ = H, or
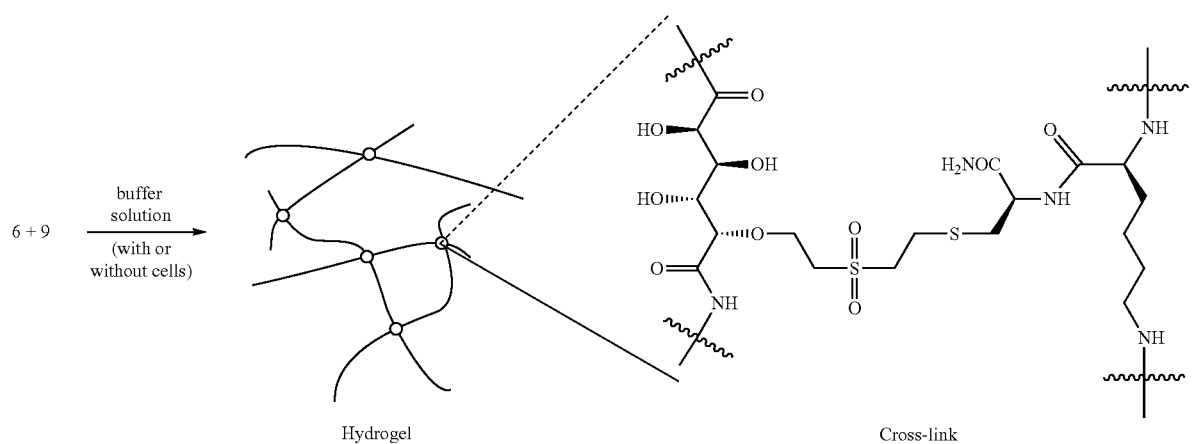
Scheme VII
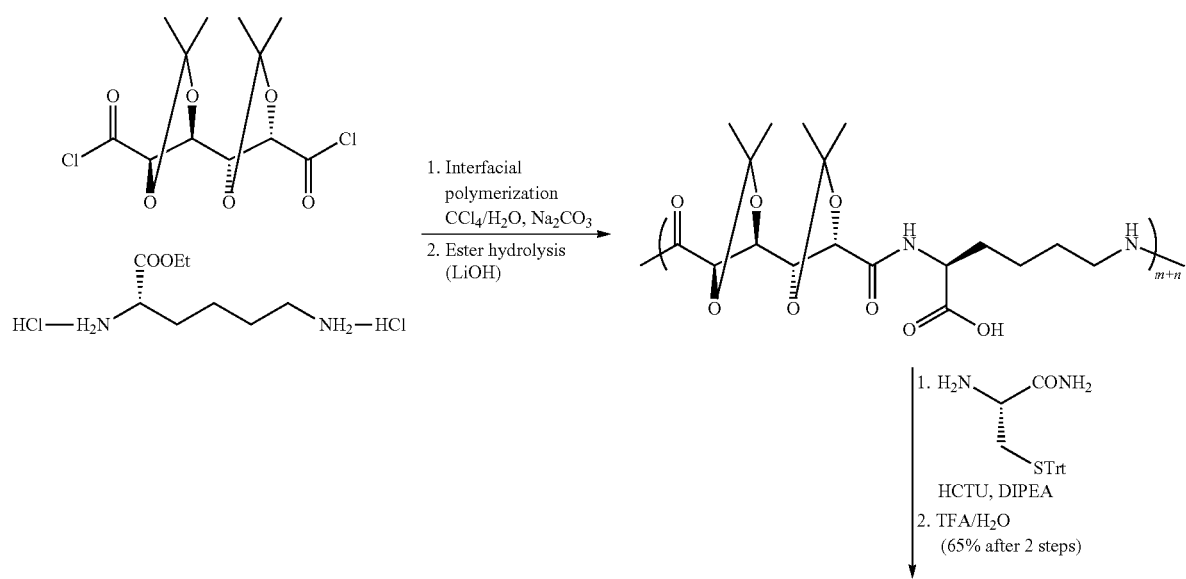

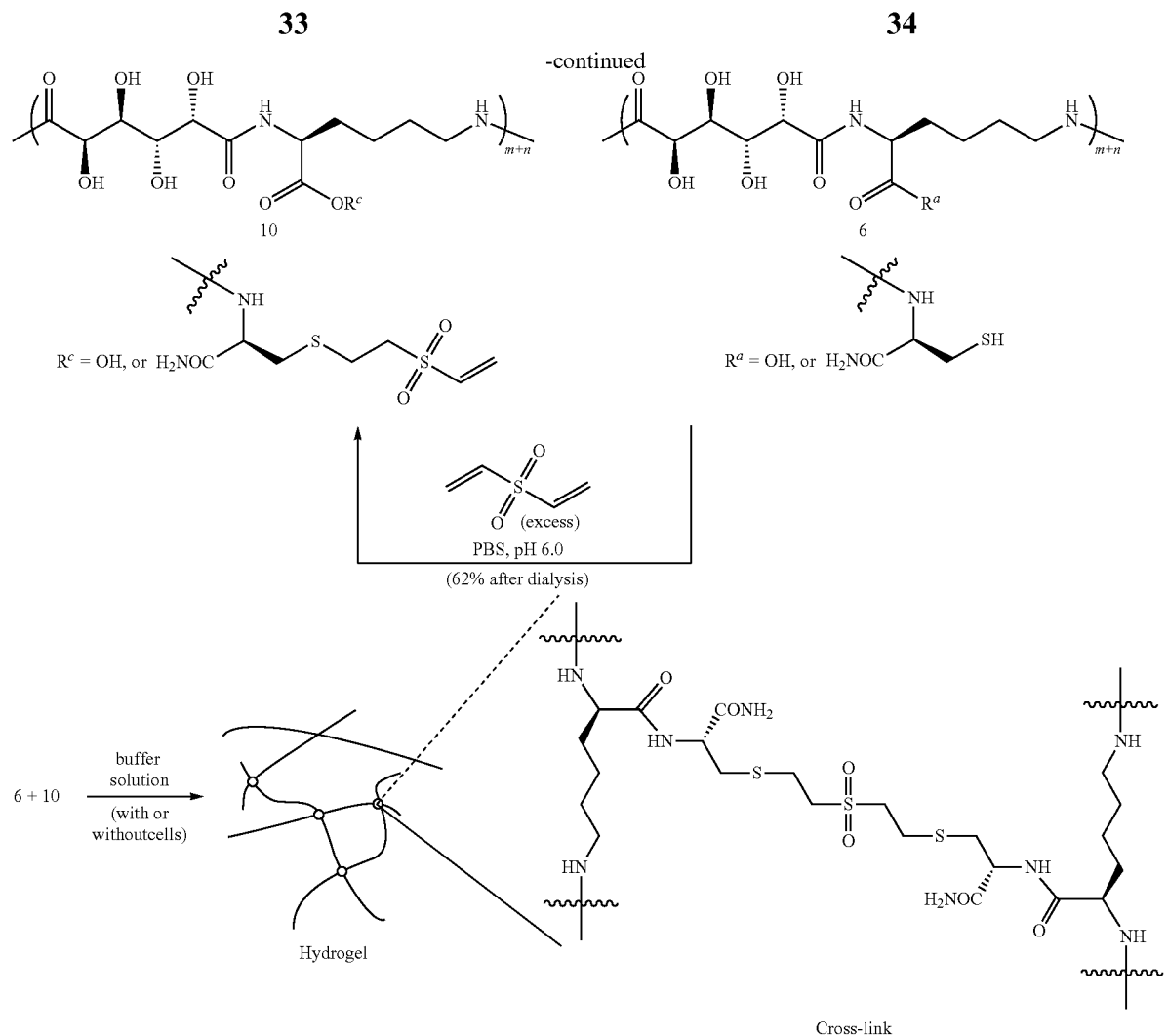

Selection of Islet Adhesive Peptide Ligands. Integrins α1β1 and α2β1 of human islets have been shown to bind to the GFOGER (L1; SEQ ID NO:6) and GAOGER (L2; SEQ ID NO:7) sequences in Collagen IV. For human islet-laminin interactions, a recent study has shown that human integrins α3β1 and α6β1 selectively bind to AGQWHRVSVRWG (L3; SEQ ID NO:8) and TWSQKALHHRVP (L4; SEQ ID NO:9) sequences derived from mouse Laminin-α5. Accordingly, these four peptides (L1-L4) are used to functionalize the SP based hydrogels for islet encapsulation.

Synthesis of the selected peptide ligands. The peptides are prepared by solid phase peptide synthesis (SPPS) using conventional Fmoc protocols. The peptide ligands are incorporated into SP based hydrogels either (a) on polymer main chain or (b) on side chain.

For main chain incorporation: a L-lysine residue is introduced to the C-terminus of each peptide. The two amino groups on the peptides, the N-terminal $NH_2$ and the ε-$NH_2$ of the C-terminal lysine residue, are utilized for copolymerization with the saccharide/L-lysine monomers (e.g., see Schemes I-IV).

For side chain conjugation: a cysteine residue is introduced to the N-terminus of each peptide. The thiol side group on terminal cysteine provides a convenient handle for covalent conjugation to SP based hydrogels. The final peptides are purified by automatic flash chromatography and/or HPLC and characterized by mass spectrometry (MS) and NMR.

Functionalization of SP Based hydrogels with Biomimetic ECM Peptides. For main chain incorporation: the ECM-derived peptide ligands are copolymerized with the saccharide/L-lysine monomers. The resulting copolymers are functionalized with either cysteine or vinyl sulfone following the procedures presented herein (e.g., Schemes I-IV). Mixing the two functionalized polymers forms functional SP based hydrogels.

For side chain grafting: the cysteine-terminated peptides as prepared above are added simultaneously with the Cys-polymer (2) and VS-polymer (3) during hydrogelation. The total molarity of cysteine is maintained equal to that of vinyl sulfone. The density of the peptide ligands in both main chain and side chain functionalization is varied from 0.05 to 5 mM. The SP based hydrogels are functionalized with the selected peptide ligands both individually and combinatorially to probe synergistic effects of multiple cell-matrix interactions.

Evaluating ECM reconstruction, islet survival and function in vitro. Human or rat islets are encapsulated in functionalized SP based hydrogels and cultured in vitro using the methods presented herein. Un-encapsulated islets from the same donor and those encapsulated in un-functionalized SP based hydrogels are used as negative controls. Cultured islets are evaluated for viability, function and presence of secreted ECM. Islet viability is evaluated and compared on day 0, 3, 7, and 14 using propidium iodide (PI) staining. Media are collected on day 1, 3, 7, 14 and monitored for changes in secreted insulin. Dynamic insulin release in response to continuous flow of different glucose concentrations is assessed on week 4 using a perifusion system. To determine the effect of various ECM ligands on promoting native ECM recovery, islets are evaluated using immunohistochemistry and immunofluorescence. In vitro ECM synthesis is followed by examining islets on day 0, 1, 3, 7 and 14 for various ECM components, and compared to ECM distribution found in the pancreas. Changes in ECM gene and protein expression are confirmed through RT-PCR and western blot, respectively. To determine the effect of adhesive ligands on ECM recovery, various signaling cascades that are influenced by cell-ECM binding, such as FAK, AKT, and ERK, are examined using western blot to confirm the mechanism of action for specific ligands.

Determining in vivo islet function and survival by subcutaneous transplantation. The two best performing functionalized SP based hydrogels determined from above are further tested in vivo. Hydrogel encapsulated rat islets are transplanted by injection into syngeneic recipients made diabetic with STZ. Islets are transplanted into the pinna of recipients. Grafts are removed on day 2, 4, 7, and 14 and examined by immunohistochemistry for the recovery of ECMs in vivo. Factors critical for evaluating islets are: (1) the impact of hydrogel on ECM recovery, (2) time required for ECM recovery, and (3) the type of ECM that is produced after transplantation. If functionalized SP-hydrogel facilitates ECM recovery, islets in functionalized SP-hydrogel are transplanted into a SC site on the abdomen, and blood glucose is monitored. The effectiveness of functionalized SP hydrogel is assessed by determining the minimum effective islet number that achieves diabetes reversal. Since 600 islets is the minimum effective number in the liver, 1000-1200 islets are expected to be effective in SC site. Therefore, 1000, 1500 and 2000 islets are tested by the 3+3 design method.

Synthesis of anti-inflammatory SP based hydrogels by conjugating anti-inflammatory agents. Covalent grafting of cytokine-antagonizing peptides onto SP based hydrogels: Previous studies have identified peptide sequences YCWSQYLCY (in disulfide form; SEQ ID NO:10) and AYC(acm)RDGKIGPPKLDIRKEEKQI (acm: acetamidomethyl; SEQ ID NO:11) as potent antagonists for TNF-α and IFN-γ, respectively. These two antagonizing peptides are covalently attached to SP based hydrogel. The two peptides are synthesized by standard SPPS, with the N-terminus finally coupled to a maleimide (MA) motif so as to provide a convenient handle for covalent attachment to the SP based hydrogels. To form functional SP based hydrogels, the Cys-polymer are first mixed with VS-polymer ([Cys]/[Vs]=1.1) for hydrogelation (e.g., see Schemes IV and V). The residual Cys groups on the formed hydrogel are used for grafting the antagonizing peptides through incubating the MA-terminated peptides with the hydrogel (with the peptide concentration 1-100 μM). The SP based hydrogel is functionalized with the two peptides either separately or in combination to probe synergistic effects. The efficacy of the functionalized SP based hydrogels for binding soluble cytokines (TNF-α and IFN-γ) is assayed by incubating the hydrogels with known amount of recombinant cytokines followed by measuring the medium cytokine level by ELISA. Based on this result, the optimal functionalization density is used for further studies.

Covalent conjugation of cytokine antibodies to SP based hydrogels. An orthogonal approach is used to conjugate monoclonal antibodies for cytokines onto SP based hydrogels to suppress inflammatory response. A heterodifunctional N-hydroxysuccinimide-PEG-acrylate (NPA, MW=3400 g/mol, BOC Sciences) are used to conjugate Etanercept (Enbrel®), a clinically used monoclonal antibody for TNF-α, and a commercially available monoclonal antibody for IFN-γ. To form functional SP based hydrogels, NPA is first reacted with Cys-polymer (2) ([NPA]/[Cys] ratio of 1/50-1/1000) followed by mixing with VS-polymer (3) for hydrogelation (e.g., see Scheme 2). The molarity of Cys is maintained so as to be equal to the combined molarity of VS and NPA. The formed SP-hydrogel is incubated with Etanercept and/or an IFN-γ antibody. The antibodies are conjugated to the hydrogel through amide bond formation between the surface amines on the proteins and the NHS ester groups from NPA. The two antibodies are either conjugated separately or in combination to probe synergistic effects. The efficacy of the functionalized SP based hydrogels for capturing soluble cytokines (TNF-α and IFN-γ) are assayed by incubating the hydrogels with known amount of recombinant cytokines followed by measuring the medium cytokine level by ELISA. Based on the results of this assay, the optimized functionalization density is used for further studies. The anti-inflammatory effects for the two approaches, i.e., conjugation of antagonizing peptides or monoclonal antibodies, are compared. If both are effective, the SP based hydrogel is functionalized with both the antagonizing peptides and antibodies to maximize the anti-inflammatory effects.

PUMA and INS Pre-mNRA as markers for islet health in response to cytokine insults. Inflammation mediated proinflammatory cytokines, including Tumor necrosis factor (TNF)-α, Interleukin(IL)-1β, Interferon (IFN)-γ, play an important role on β cell death, leading to primary graft nonfunction. TNF-α transcriptionally upregulates a proapoptotic gene, PUMA (p53 upregulated modulator of apoptosis) in human islets through the activation of nuclear factor kappa B (NF-κB) in vitro. While TNF-α alone did not induce severe β cell damage, its combination with IFN-γ induced a substantial increase in β cell death. Elevated PUMA mRNA by TNF-α or the TNF-α+ and IFN-γ combination correlated with decreased islet function, as indicated by decreased preproinsulin (INS) pre-mRNA expression (r=−0.45, p<0.001) assessed by the single islet gene expression assay (RT-PCR). TNF-α receptor blocker, Etanercept, abolished TNF-α mediated PUMA mRNA up-regulation in human islets. PUMA mRNA and INS pre-mRNA expressions are used herein as markers for islet health under cytokine insults.

Examining the islet protective effect of SP based hydrogels grafted with cytokine-antagonizing peptides. Islets encapsulated within the SP based hydrogels functionalized with TNF-α and/or IFN-γ antagonizing peptides are cultured with known dose of corresponding recombinant (r) TNF-α and/or rIFN-γ. In pilot study, Luc(+) rat islets are used to monitor viability by luminescence imaging for up to 2 weeks. Positive results are further confirmed using Luc (−) rat islets by using the following studies. Expression level of PUMA mRNA and CXCL10 mRNA in islets are measured by RT-PCR to determine the suppression of cytokine mediated islet damage by functionalized SP based hydrogels. PUMA mRNA is used as an indicator for TNF-α signaling and CXCL10 mRNA as an indicator for IFN-γ signaling. Islet viability is examined by PI staining, insulin staining, and TUNEL staining (β cell apoptosis). Islet function is tested by a dynamic insulin release assay in a perifusion system and insulin synthesis in human islets by INS pre-mRNA assay.

Examining the islet protective effect of SP based hydrogels conjugated with antibodies. Islets are encapsulated with SP based hydrogels conjugated with TNF-α and/or IFN-γ antibodies and cultured with corresponding recombinant cytokines. The effects of functionalized SP based hydrogels are determined by the methods described above.

Examining the synergistic effect of antagonizing peptides and antibodies. Islets are encapsulated in SP based hydrogels having both covalently attached antagonizing peptides and antibodies. The effects of functionalized SP based hydrogels on islet protection are determined by the methods described above.

In Vitro Biocompatibility Assay of SP Hydrogel by Stimulation Assay of Peripheral Blood Mononuclear Cells (PBMC). PBMC from a normal LEW rat were isolated using Histopaque (Sigma-Aldrich, St. Louis, Mo.). $1\times10^6$ Cells were incubated with either 0.5 µL phosphate buffered saline (PBS), 0.5 mg vicryl suture, 0.5 mg hydrogel, 0.5 mg VS-polymer, 0.5 mg Cys-polymer, or 5 µg of LPS for 20 hours at 37° C. Differences in Ct between the target and control (Actb) mRNA ($\Delta$Ct) were used to quantify the relative level for each sample's mRNA expression.

In vitro examination of functionalized SP-hydrogel using peripheral blood mononuclear cells (PBMC). Rat or human islets are encapsulated in functionalized hydrogels and incubated with PBMC prepared from the syngeneic rat or same donor blood without alloantigen involvement. After 24 and 48 hours of incubation, PBMC activation is assessed by RT-PCR for inflammatory gene expression, including TNF-α, IFN-γ, CXCL1, IL1, IL6, and GMCSF. Results are compared to those obtained with islet alone, PBMC alone, and functionalized hydrogel alone. β cell apoptosis and function are examined as described above. The most effective anti-inflammatory SP based hydrogels are then determined by using the in vitro studies described above.

Evaluating in vivo anti-inflammatory SP-hydrogel function for prevention of islet loss. The anti-inflammatory SP based hydrogels selected from above is used in vivo to examine the islet protective effect from inflammation associated with islet transplantation.

Determining a minimum number of islets effective for diabetes reversal in syngeneic recipients. A known number of islets isolated from Lewis rats are encapsulated in SP based hydrogels covalently functionalized with (1) cytokine-antagonizing peptides, (2) cytokine antibodies, or (3) both peptides and antibodies and then transplanted subcutaneously in syngeneic rats made diabetic with streptozotocin (STZ). The minimum number of islets effective for diabetes reversal are determined as described above. The hydrogel that has reversed diabetes with the smallest islet number is considered the most effective anti-inflammatory SP-hydrogel and is used in further studies.

Islets encapsulated with the best performed SP-hydrogel are subcutaneously transplanted in syngeneic recipient for immunohistochemical studies. The graft is biopsied after 6, 12, 24 and 48 hours to examine the apoptosis of the cells by immunohistochemistry. Cytokine responses in the graft are assessed by in situ gene expression.

A one-step SC transplantation protocol using islet and VEGF-MSC co-encapsulation in an unmodified SP-hydrogel. Results with Luc(+) firefly rat islets indicated that <30% of islets without hydrogel and >70% of encapsulated islets survive 7 days after SC placement, demonstrating the advantage of SP based hydrogel encapsulation for SC islet transplantation. To further confirm these results, 1000 Luc(+) islets are SC transplanted with or without SP based hydrogel into syngeneic, Luc(−) Lewis rats made diabetic with STZ. Islets survival is assessed by Xenogen imaging following d-luciferin salt (30 mg/kg) injection. The blood glucose levels and serum C-peptide released to high glucose stimulation is also measured. In this study, diabetes reversal is not the primary objective, but blood glucose would be expected to decrease with islets encapsulated in hydrogel in comparison to control.

Optimization of VEGF release kinetics from SP-hydrogel encapsulated VEGF-MSC. High transfection efficiency (>90%) using electroporation was found using GFP-VEGF121. ELISA is used to measure VEGF release (24 hour) from an established number of VEGF-MSCs encapsulated in SP based hydrogels. The results are then used to determine a suitable number of VEGF-MSCs to be co-encapsulated with islets. 100 ng/mL of VEGF is usually used to construct pre-vascularized graft bed. Accordingly, this dose is used with the procedures presented herein but may be modified based upon results.

Determining the effect of co-encapsulated VEGF-MSCs on islet revascularization in vivo. SP based hydrogels containing VEGF-MSCs and islets, or appropriate controls are injected in a syngeneic rat pinna. The effect of VEGF-MSCs on neovascularization kinetics is determined by image analysis (Prairie Technologies Ultima 2-photon microscope) of the transplant site following an IV injection (200 mg/kg) of FITC-dextran to visualize vascular formation. It is anticipated that the vascularization will be significantly better with the SP based hydrogel containing VEGF-MSCs as compared to those containing naïve or no MSCs. The optimal VEGF-MSC number/concentration to achieve rapid and rich vascularization is further determined.

Determining the function and survival of subcutaneously transplanted islets co-encapsulated with VEGF-MSCs in functionalized sp based hydrogels. Islets and VEGF-MSCs are encapsulated at the ratio determined above. The volume of the hydrogel is limited to being as small as possible and the approximate total volume will not exceed 50 µL. Islets and VEGF-MSCs are injected through a #23 gauge needle in SC on the abdomen of syngeneic Lewis rats made diabetic with STZ. (1) The minimum effective number of islets are determined as described above. Blood glucose, plasma C-peptide levels, and periodic glucose tolerance tests are performed in euglycemic recipients for up to 6 months, at which time grafts are removed and histologically examined. (2) To determine the influence of SC location, the minimal effective islet number is encapsulated in the same method and transplanted SC on the dorsal area, where the skin is thickest, and flank, which has less subcutaneous tissue. (3) The minimum effective number of Luc(+) islets and VEGF-MSCs from Luc(−) Lewis rats are co-encapsulated at the optimal ratio in functionalized SP based hydrogels and a total volume of approximately 50 µL are transplanted into a SC site on the flank of Luc(−) diabetic Lewis rats. Islet viability is assessed by Xenogen imaging, 3 times a week for 2 weeks. Changes in viable islet mass and progress of vascularization is approximated based on changes in luminescent activity. Two weeks after grafting, vascularization is examined by MRI and compared to appropriate controls. This test also reveals the effect of diabetes on neovascularization by comparing images taken from diabetic and non-diabetic recipients. Islets co-encapsulated with VEGF-MSCs are expected to show the best vascularization.

Determining human islet survival and function following co-encapsulation with VEGF-MSCs in functionalized SP-hydrogel and subcutaneous transplantation into diabetic NODscid mice. Human MSCs (hMSCs) have been shown to be effective in numerous clinical trials and can be successfully isolated and expanded from adipose tissue. hMSCs of recipient origin are prepared from biopsied adipose tissue and cryopreserved. hMSCs of donor origin are prepared from peri-pancreatic adipose tissue. VEGF-hMSCs are generated through the transfection method developed for rat MSCs.

Human islets and VEGF-hMSCs are co-encapsulated in functionalized SP-hydrogel in <50 µL and injected using #23 gauge needle in SC on the dorsal side of diabetic NODscid mice. Since 1000 human islets transplanted in the space under the renal capsule routinely reverse diabetes, 1500, 1000, and 800 islet numbers are tested to determine the minimally effective islet number. Recipient mice are monitored up to 3 months for blood glucose levels (weekly), serum human C-peptide levels (monthly), and glucose tolerance test at the end of study. The grafts are recovered for immunohistochemical examination.

In vitro examination of functionalized SP-hydrogel using peripheral blood mononuclear cells (PBMC). Rat or human islets are encapsulated in functionalized hydrogels and incubated with PBMC prepared from the syngeneic rat or same donor blood without alloantigen involvement. After 24 and 48 hours of incubation, PBMC activation is assessed by RT-PCR for inflammatory gene expression, including TNF-α, IFN-γ, CXCL1, IL1, IL6, and GMCSF. Results are compared to those obtained with islet alone, PBMC alone, and functionalized hydrogel alone. β cell apoptosis and function are examined as described above. The most effective anti-inflammatory SP based hydrogels are then determined by using the in vitro studies described above.

Evaluating in vivo anti-inflammatory SP-hydrogel function for prevention of islet loss. The anti-inflammatory SP based hydrogels selected from above is used in vivo to examine the islet protective effect from inflammation associated with islet transplantation.

Determining a minimum number of islets effective for diabetes reversal in syngeneic recipients. A known number of islets isolated from Lewis rats are encapsulated in SP based hydrogels covalently functionalized with (1) cytokine-antagonizing peptides, (2) cytokine antibodies, or (3) both peptides and antibodies and then transplanted subcutaneously in syngeneic rats made diabetic with streptozotocin (STZ). The minimum number of islets effective for diabetes reversal are determined as described above. The hydrogel that has reversed diabetes with the smallest islet number is considered the most effective anti-inflammatory SP-hydrogel and is used in further studies.

Islets encapsulated with the best performed SP-hydrogel are subcutaneously transplanted in syngeneic recipient for immunohistochemical studies. The graft are biopsied after 6, 12, 24 and 48 hours to examine the apoptosis of the cells by immunohistochemistry. Cytokine responses in the graft are assessed by in situ gene expression.

A one-step SC transplantation protocol using islet and VEGF-MSC co-encapsulation in an unmodified SP-hydrogel. Results with Luc(+) firefly rat islets indicated that <30% of islets without hydrogel and >70% of encapsulated islets survive 7 days after SC placement, demonstrating the advantage of SP based hydrogel encapsulation for SC islet transplantation. To further confirm these results, 1000 Luc(+) islets are SC transplanted with or without SP based hydrogel into syngeneic, Luc(−) Lewis rats made diabetic with STZ. Islets survival is assessed by Xenogen imaging following d-luciferin salt (30 mg/kg) injection. The blood glucose levels and serum C-peptide released to high glucose stimulation is also measured. In this study, diabetes reversal is not the primary objective, but blood glucose would be expected to decrease with islets encapsulated in hydrogel in comparison to control.

Optimization of VEGF release kinetics from SP-hydrogel encapsulated VEGF-MSC. High transfection efficiency (>90%) using electroporation was found using GFP-VEGF121. ELISA is used to measure VEGF release (24 hour) from an established number of VEGF-MSCs encapsulated in SP based hydrogels. The results are then used to determine a suitable number of VEGF-MSCs to be co-encapsulated with islets. 100 ng/mL of VEGF is usually used to construct pre-vascularized graft bed. Accordingly, this dose is used with the procedures presented herein but may be modified based upon results.

In Vivo Biocompatibility Assessment of SP Hydrogel. VS-polymer and Cys-polymer were mixed to a total volume of 20 µL, aspirated in a 1 mL syringe, and then injected into the pinna of non-diabetic LEW rats prior to gelation. In the opposite pinna, the same amount of PBS was injected. The pinnas were excised on day 0 and 13 for preparation of histological slides. Samples were fixed in 10% formalin overnight and embedded in paraffin. The samples were then sectioned, and stained with hematoxylin and eosin (H&E) stains. Results were documented by bright field microscopy using an Olympus BX51.

In Vivo Survival rate of Hydrogel Encapsulated Islets in Syngeneic Rats. Islets were encapsulated in a SP hydrogel and transplanted into various extrahepatic sites of euglycemic syngeneic LEW recipients. Reversal of diabetes was tested by transplanting encapsulated islets in two different sites: (1) under the renal capsule, and (2) a pocket made by the omentum. Recipient rats were treated with streptozotocin (65 mg/kg, Sigma-Aldrich) via tail vein injection at day 7 before transplantation. Diabetes was confirmed by blood glucose levels higher than 350 mg/dL for two consecutive measurements. Diabetic rats were transplanted with 500 islets with or without hydrogel. After transplantation, blood glucose was measured twice a week to monitor islet graft function.

Transfection of VEGF expressing plasmid to MSCs derived from rat adipose tissue. MSCs were prepared by culturing cells obtained from collagenase-digested adipose tissue. The morphology, ability to differentiate into adipocytes, chondrocytes and osteoblasts, and suppression of mitogenstimulated lymphocyte proliferation were used to characterize MSCs. We have also tested transfection of MSCs by electroporation using Neon Transfection System (Invitrogen). Pilot results with FITC-VEGF plasmid indicated as high as 95% transfection rate was achieved by this method.

Determining the effect of co-encapsulated VEGF-MSCs on islet revascularization in vivo. SP based hydrogels containing VEGF-MSCs and islets, or appropriate controls are injected in a syngeneic rat pinna. The effect of VEGF-MSCs on neovascularization kinetics is determined by image analysis (Prairie Technologies Ultima 2-photon microscope) of the transplant site following an IV injection (200 mg/kg) of FITC-dextran to visualize vascular formation. It is anticipated that the vascularization will be significantly better with the SP based hydrogel containing VEGF-MSCs as compared to those containing naïve or no MSCs. The optimal VEGF-MSC number/concentration to achieve rapid and rich vascularization is further determined.

Determine the function and survival of subcutaneously transplanted islets co-encapsulated with VEGF-MSCs in functionalized SP based hydrogels: Islets and VEGF-MSCs are encapsulated at the ratio determined above. The volume of the hydrogel is limited to being as small as possible and the approximate total volume will not exceed 50 µL. Islets and VEGF-MSCs are injected through a #23 gauge needle in SC on the abdomen of syngeneic Lewis rats made diabetic with STZ. (1) The minimum effective number of islets are determined as described above. Blood glucose, plasma C-peptide levels, and periodic glucose tolerance tests are performed in euglycemic recipients for up to 6 months, at which time grafts are removed and histologically examined. (2) To determine the influence of SC location, the minimal effective islet number is encapsulated in the same method and transplanted SC on the dorsal area, where the skin is thickest, and flank, which has less subcutaneous tissue. (3) The minimum effective number of Luc(+) islets and VEGF-MSCs from Luc(−) Lewis rats are co-encapsulated at the optimal ratio in functionalized SP based hydrogels and a total volume of approximately 50 μL is transplanted into a SC site on the flank of Luc(−) diabetic Lewis rats. Islet viability is assessed by Xenogen imaging, 3 times a week for 2 weeks. Changes in viable islet mass and progress of vascularization is approximated based on changes in luminescent activity. Two weeks after grafting, vascularization is examined by MRI and compared to appropriate controls. This test also reveals the effect of diabetes on neovascularization by comparing images taken from diabetic and non-diabetic recipients. Islets co-encapsulated with VEGF-MSCs are expected to show the best vascularization.

Determining human islet survival and function following co-encapsulation with VEGF-MSCs in functionalized SP-hydrogel and subcutaneous transplantation into diabetic NODscid mice: Human MSCs (hMSCs) have been shown to be effective in numerous clinical trials and can be successfully isolated and expanded from adipose tissue. hMSCs of recipient origin are prepared from biopsied adipose tissue and cryopreserved. hMSCs of donor origin are prepared from peri-pancreatic adipose tissue. VEGF-hMSCs are generated through the transfection method developed for rat MSCs. Human islets and VEGF-hMSCs are co-encapsulated in functionalized SP-hydrogel in <50 μL and injected using #23 gauge needle in SC on the dorsal side of diabetic NODscid mice. Since 1000 human islets transplanted in the space under the renal capsule routinely reverse diabetes, 1500, 1000, and 800 islet numbers are tested to determine the minimally effective islet number. Recipient mice are monitored up to 3 months for blood glucose levels (weekly), serum human C-peptide levels (monthly), and glucose tolerance test at the end of study. The grafts are recovered for immunohistochemical examination.

Statistical Analysis: Data are reported as mean±standard error (SEM). Effects of time and the presence or absence of SP hydrogel were assessed by student t-test. $P<0.05$ denotes statistical significance.

Ex vivo biocompatibility of soluble polymers and SP hydrogel: An SP hydrogel was formed by in situ crosslinking by mixing a cysteine-functionalized (Cys-polymer) and a vinyl sulfone-functionalized (VS-polymer) saccharide-peptide copolymer under mild conditions, according to protocols presented in Chawla et al., *Biomacromolecules* (2011) 12:560-567, and Chawla et al., *Biomaterials* (2012) 33:6052-6060, which are incorporated herein in their entirety. To evaluate possible cytokine activation caused by the hydrogel and its individual polymer components, rat PBMCs were incubated in vitro with Cys-polymer, VS-polymer, SP hydrogel, negative controls, PBS or vicryl suture, or a positive control, lipopolysaccharide (LPS), for 18 hours in a tissue culture incubator. The mRNA expression of inflammatory cytokines released by PBMC, including TNF-α (killer cell), IFN-γ (T-cell activation), CXCL1 (IL-8 analog, recruiter), IL6 (killer cell), and GMCSF (antigen presentation) was assessed to detect any immune stimulatory effect. LPS showed the highest stimulatory effect. Compared to LPS (positive control), PBMC exposed to other materials showed minimal mRNA response as measured by IFN-γ, CXCL1, IL6, and GMCSF mRNA levels ($p<0.05$) (see FIG. 2). Responses to SP hydrogel or the individual components were not significantly different than PBS (negative control) ($p=0.06$-$0.49$).

Evaluation of viability in hydrogel-cultured islets: Islets encapsulated in SP hydrogel and cultured in a transwell culture insert maintained normal 3D structure, whereas the 3D structure gradually degraded in non-encapsulated control islets. The viability of islets isolated from "Firefly" LEW rats (Rosa/luc LEW Tg) was evaluated through luminescence measurements taken over a 28 day period (see FIG. 3A). Luminescent activity of the islets dramatically decreased over 28 days in cultures without hydrogel encapsulation (see FIG. 3B) and the islets rapidly disintegrated ($p<0.01$). In contrast, the viability of hydrogel-encapsulated islets was maintained through day 7 and then decreased, but not significantly ($p=0.07$) (see FIG. 3B). Throughout the period, hydrogel-encapsulated islet viability was significantly higher than the control non-encapsulated islets ($p<0.05$). These data was further confirmed with qualitative images of islet viability using Live/Dead staining. Islets encapsulated in hydrogel were highly viable with intact morphology even after 28 days in culture. In contrast, unencapsulated islets aggregated and showed peripheral damage. The culture contained many dissociated single cells most of which were dead cells (See FIG. 4).

Islet glucose consumption: Glucose consumption in culture media was used to measure the metabolic activity of hydrogel encapsulated islets maintained in culture. Glucose metabolism is measured primarily by the glucose utilization in medium by the cultured islets and has been shown as an indicator not only for islet viability, but also cellular activity. The uptake of glucose in medium was measured every 48 hours over the 28 day period to assess islet quality. Glucose uptake in encapsulated islets was maintained near 100% of day 1 level until day 21 (see FIG. 5A). The level then decreased slightly to 88% on day 28, which coincided with hydrogel degradation and the gradual loss of the 3D islet structure. In control islets, by day 7 glucose consumption had decreased to 56%, and further declined as time progressed. By day 21 and 28, 34% and 25% of the glucose was utilized, respectively. Overall, encapsulated islets maintained much higher metabolic activity as compared to control islets ($p<0.01$).

Islet insulin synthesis: To quantify the biosynthetic capacity of insulin, cultured islets were incubated in either a low- (3.3 mM) or a high- (17 mM) glucose medium for 16 hours on day 0 and day 14 (see FIG. 5B). Hydrogel encapsulated islets maintained insulin secretion levels of freshly isolated islets (day 0) in both high and low glucose exposure ($p=0.21$-$0.40$). In contrast, the glucose responsiveness was not preserved in the control cultured islets tested on day 14 ($p<0.05$, vs. control on day 0 and encapsulated islets on day 14). The decreased insulin storage/secretion ability of the control islets was also shown by decreased insulin staining by dithizone (DTZ) on day 14 (see FIG. 4).

Dynamic insulin release in a perifusion system: To further assess beta cell function, dynamic glucose stimulated insulin release was tested in a perifusion system using islets cultured with or without hydrogel encapsulation for 28 days. Although the same number of islets was present in both the encapsulated and control samples on day 0, islets in the control group disintegrated over time and did not show stimulated insulin secretion. In contrast, encapsulated islets responded well to glucose stimulation (see FIG. 5C).

In vivo biocompatibility of hydrogel: To evaluate the foreign body response elicited by the hydrogel in vivo, hydrogels were injected into the rat pinna, which was later biopsied for histological examination. Sections taken on day 1 and 13 showed minimal cell infiltration into the hydrogel and surrounding area (see FIG. 6A). On day 1, the implanted hydrogel was spread out between subcutaneous tissues and remained intact. By day 13, hydrogel degradation was detectable with different shades of intermixed purple on H&E-stained sections with only few mononuclear cells found in a very confined area adjacent to hydrogel. These results indicate that SP hydrogel is highly biocompatible and biodegradable in vivo.

Figure 8:
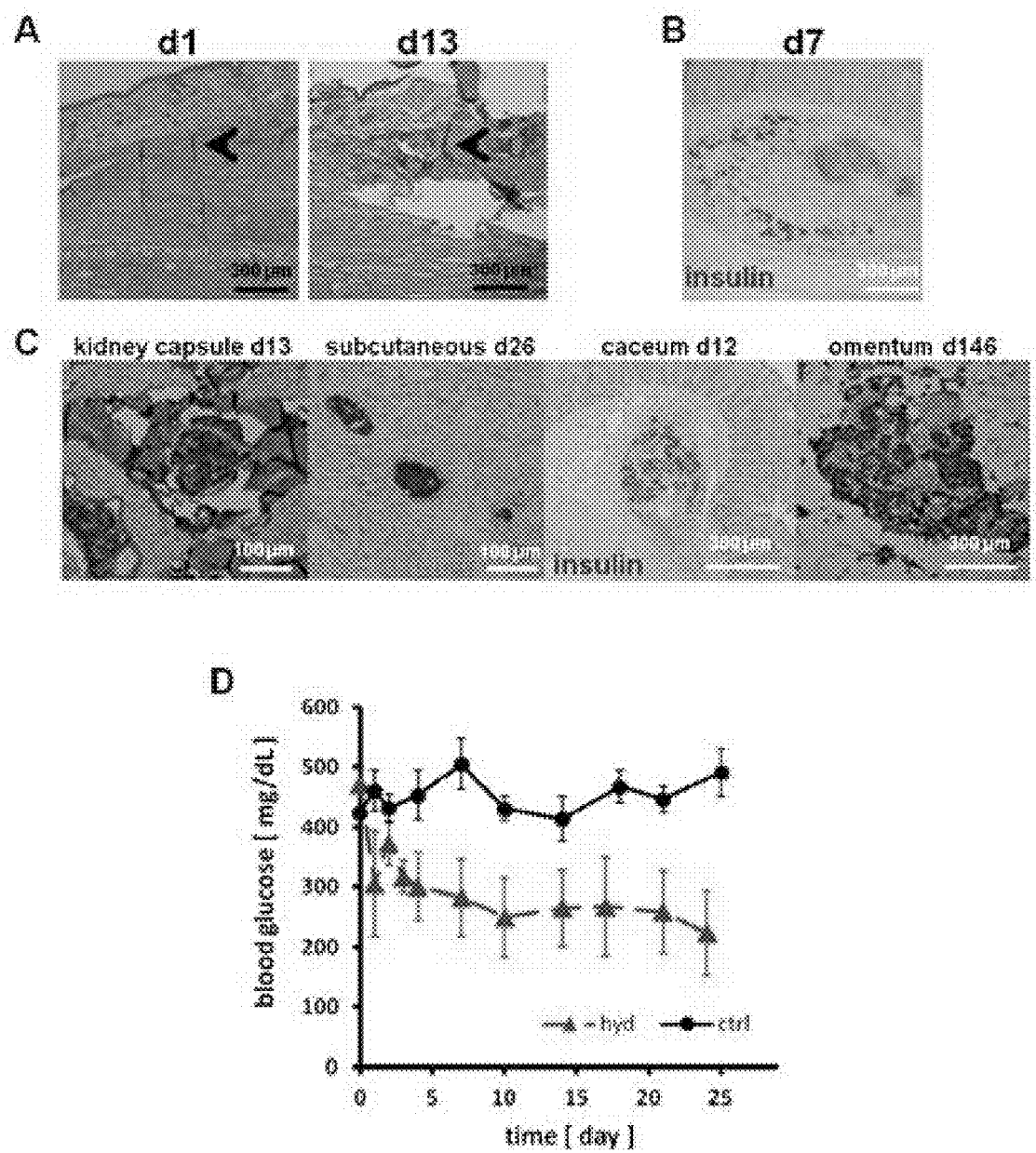
FIG. 8A-D presents in vivo biocompatibility data of a hydrogel of the disclosure on islet function. (A) Hematoxylin and eosin stain (H&E) stained histological sections of the rat pinna after 1 and 13 days of hydrogel injection. Minimal cell infiltration was observed in a small area adjacent to hydrogel (arrowheads). (B) Viable islets were scattered around the large mass of necrosis (light brown) observed after naked islets were injected under the submucosa of the stomach. (C) When transplanted with hydrogel, syngeneic islets stained positive for insulin (brown) were detected in various extrahepatic sites. (D) Blood glucose levels of diabetic rats after islet transplantation. 500 SP based hydrogel encapsulated syngeneic islets were placed in an omentum pouch on day 0 (SP hydrogel, n=4). Controls were transplanted without the hydrogel (ctrl, n=5). Islet in a SP based hydrogel lowered blood glucose levels more effectively than control islets (p<0.05).
Figure 9:
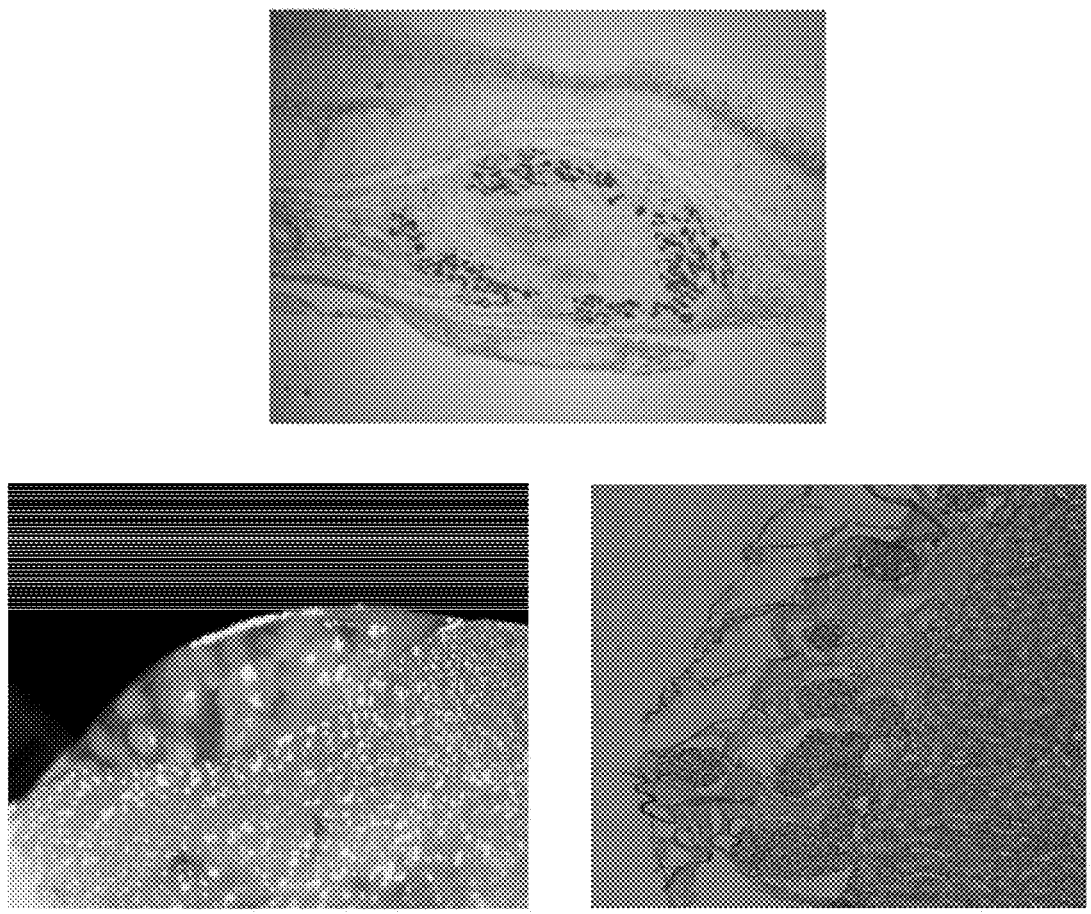
FIG. 9 presents images of extrahepatic islet transplantation. Extrahepatic implantation without hydrogel (top) leads to poor vasculature, islet clumping and necrosis, and dispersion of islets. By contrast, islets dispersed in hydrogel (bottom) when transplanted on the kidney show increased vasculature, less islet clumping, and limited dispersion.
Figure 10:
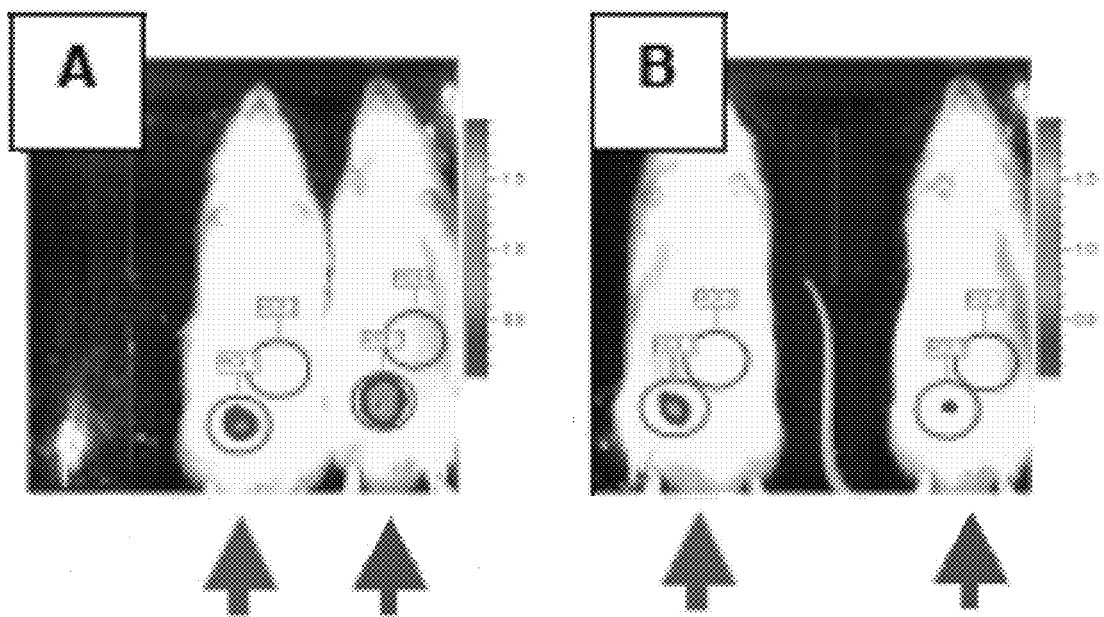
FIG. 10A-B provides for luciferase transgenic islets transplanted subcutaneously in rats with SP based hydrogel (left animal; red arrow) or unencapsulated (right animal; blue arrow) imaged on (A) day 0 and (B) day 24.
Figure 11:
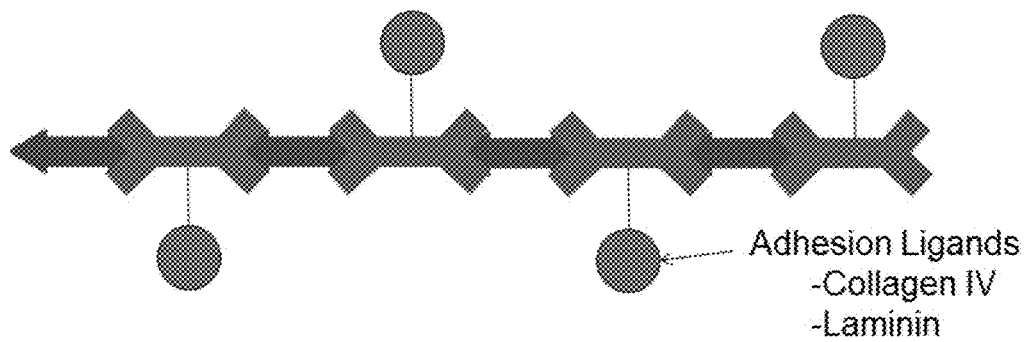
FIG. 11 presents a diagram of the functionalization of the SP based hydrogels with adhesion ligands collagen IV and laminin.
Figure 12:
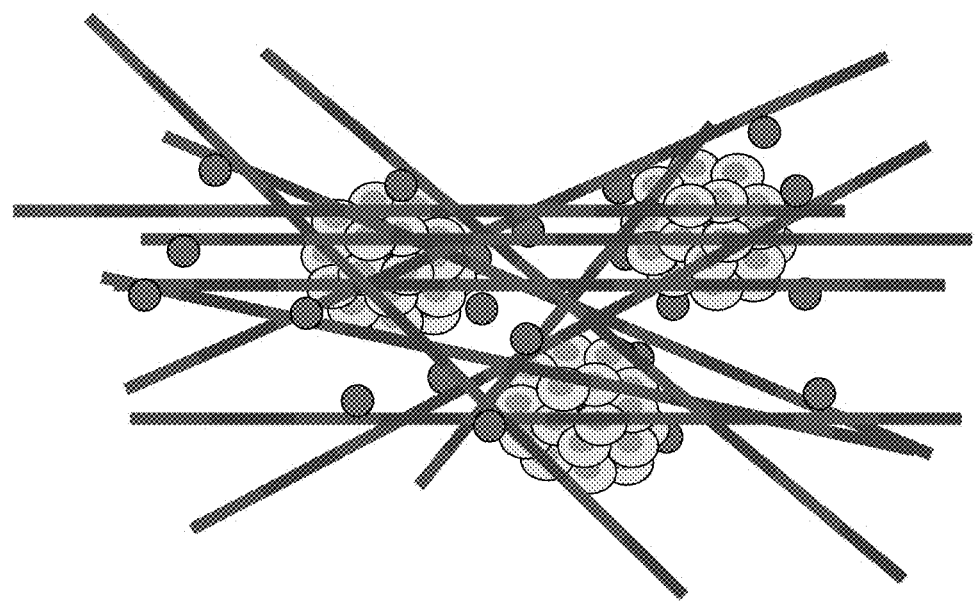
FIG. 12 presents a diagram of the encapsulation of cells within SP based hydrogels that has been functionalized with cell adhesion ligands.
Figure 13:
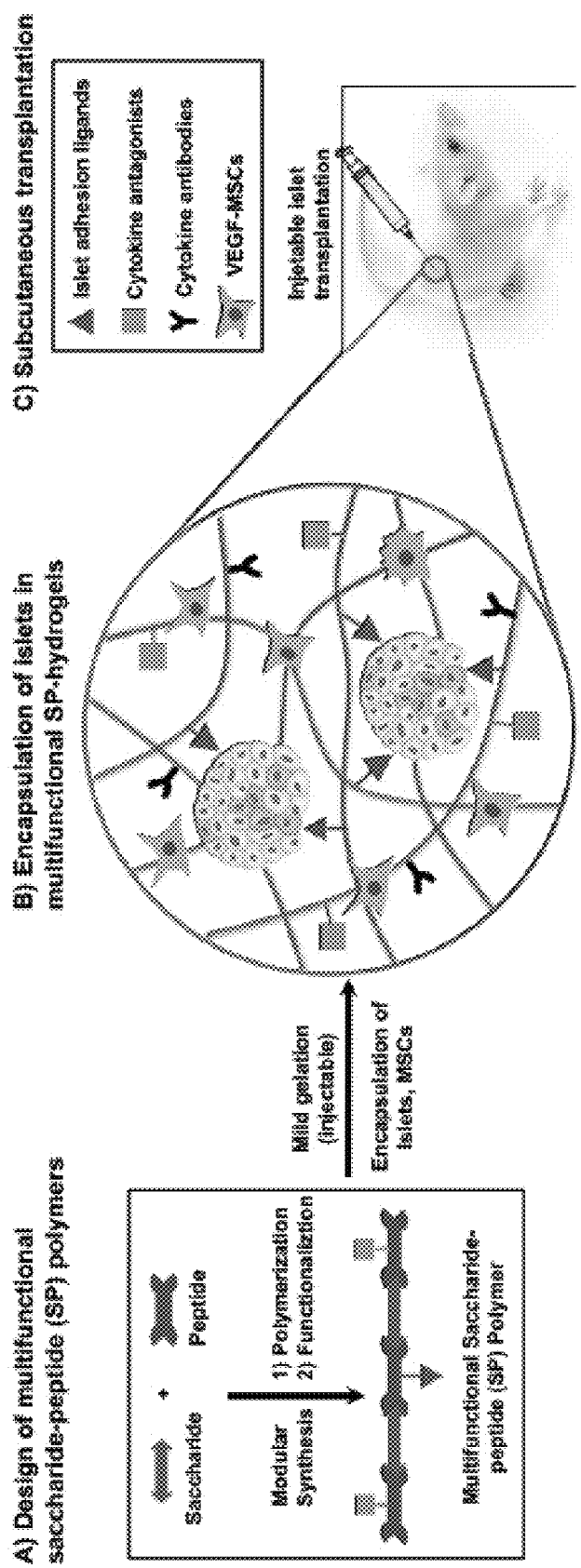
FIG. 13A-C presents multifunctionalized SP based hydrogels for improving the outcome of extrahepatic islet transplantation. (A) Saccharide-peptide based polymers are generated through interfacial polymerization. These SP-based polymers are then functionalized by attaching various ligands, including biomimetic ligands, adhesion ligands, and antagonists to cytokines. (B) Hydrogelation of the SP-based polymers in the presence of islets and mesenchymal stem cells (MSCs) results in encapsulation of the islets and MSCs in multifunctional SP based hydrogels. (C) The encapsulated islets and MSCs can then be injectably transplanted in vivo in extrahepatic sites.
Figure 14:
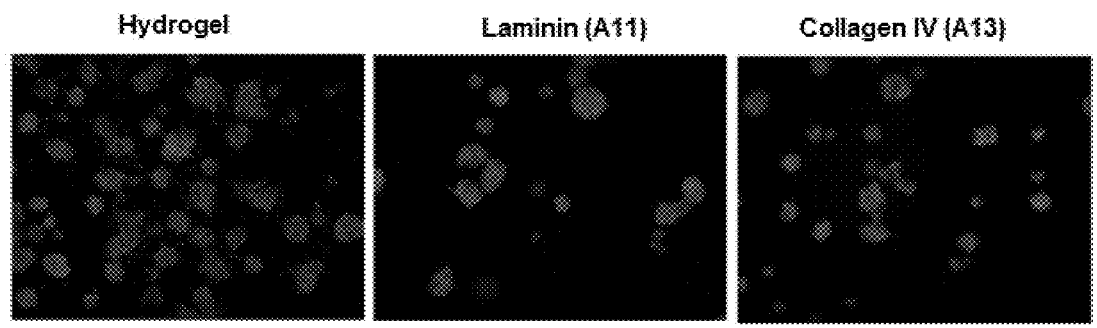
FIG. 14 demonstrates that SP based hydrogels functionalized with laminin (middle) or collagen IV (right) improve the viability of the Insulinoma cell line in vitro over nonfunctionalized SP based hydrogels (left). Cells stained red with propidium iodide indicate dead cells while cells stained green with fluorescent diacetate indicate live cells.
Figure 15:
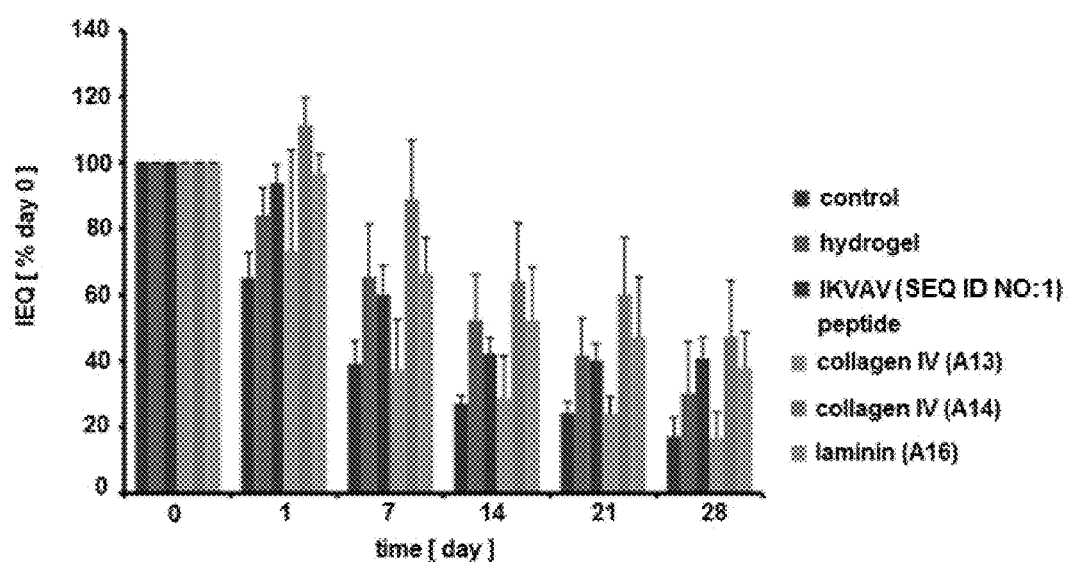
FIG. 15 provides a graph looking at the effect of hydrogel and ECM functionalized hydrogel on islet equivalent (IEQ) of human islets cultured in low glucose over a period of 28 days. In comparison to control cells, a higher IEQ was measured for hydrogel encapsulated islets, and an even higher IEQ was measured for islets encapsulated in ECM functionalized hydrogel.
Figure 16:
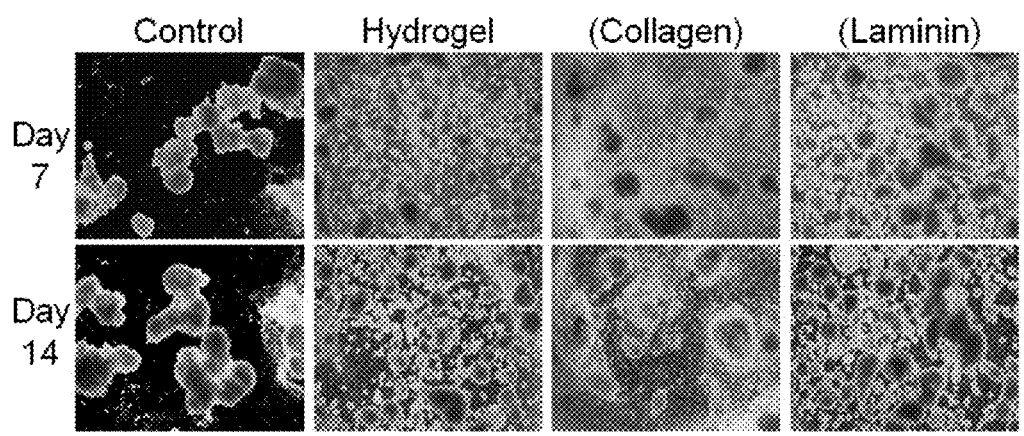
FIG. 16 provides that islets cultured in functionalized SP based hydrogel maintain morphology over 14 days.
Figure 17:
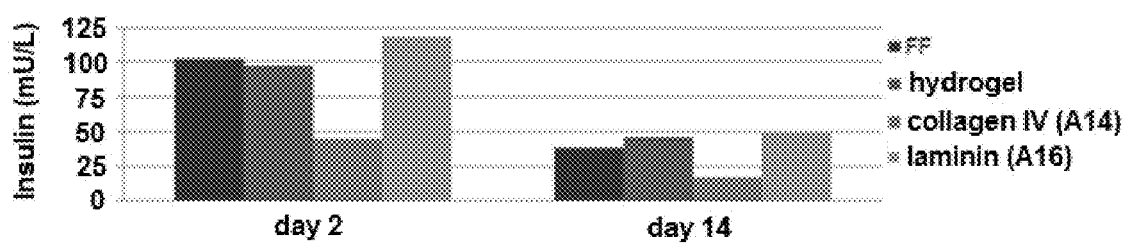
FIG. 17 provides that islets cultured in functionalized hydrogel release a measureable amount of insulin over 24 hours in vitro.
Figure 18:
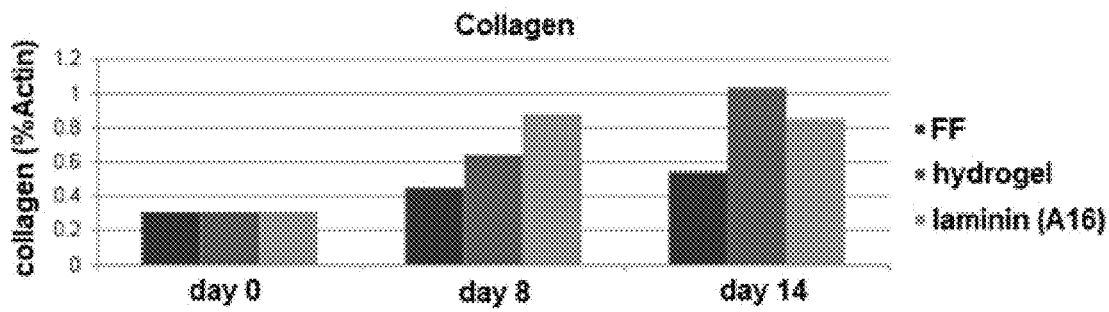
FIG. 18 provides that functionalized SP based hydrogel increases collagen expression in vitro.
Figure 19:
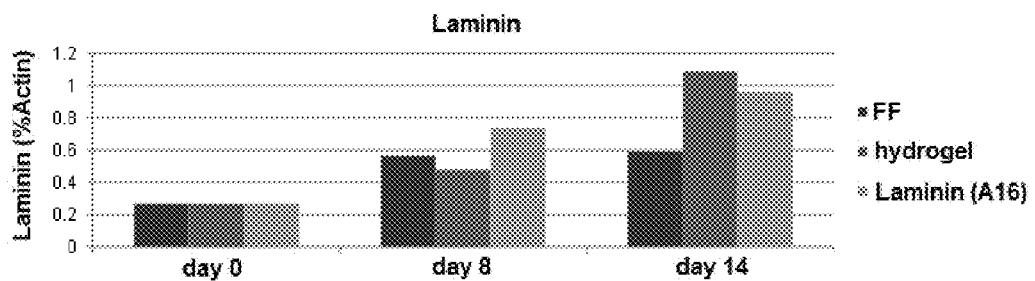
FIG. 19 provides that functionalized SP based hydrogel increases laminin expression in vitro.
Figure 20:
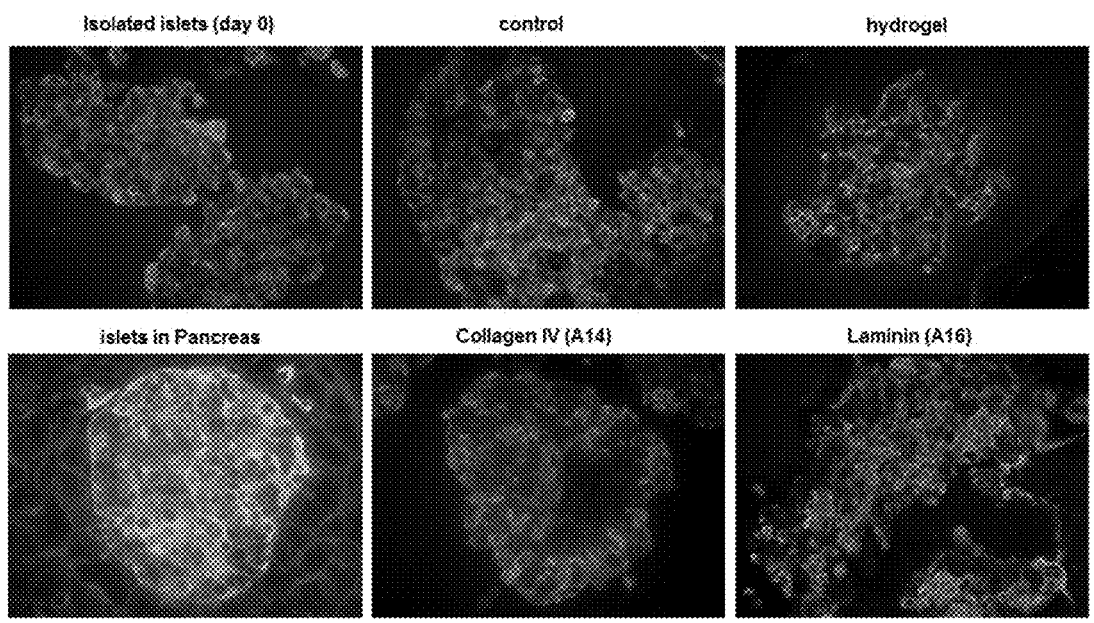
FIG. 20 demonstrates that functionalized SP based hydrogel aid in ECM reconstruction in vitro. Insulin is stained green, collagen IV is stained red, and DAPI is blue.
Figure 21:
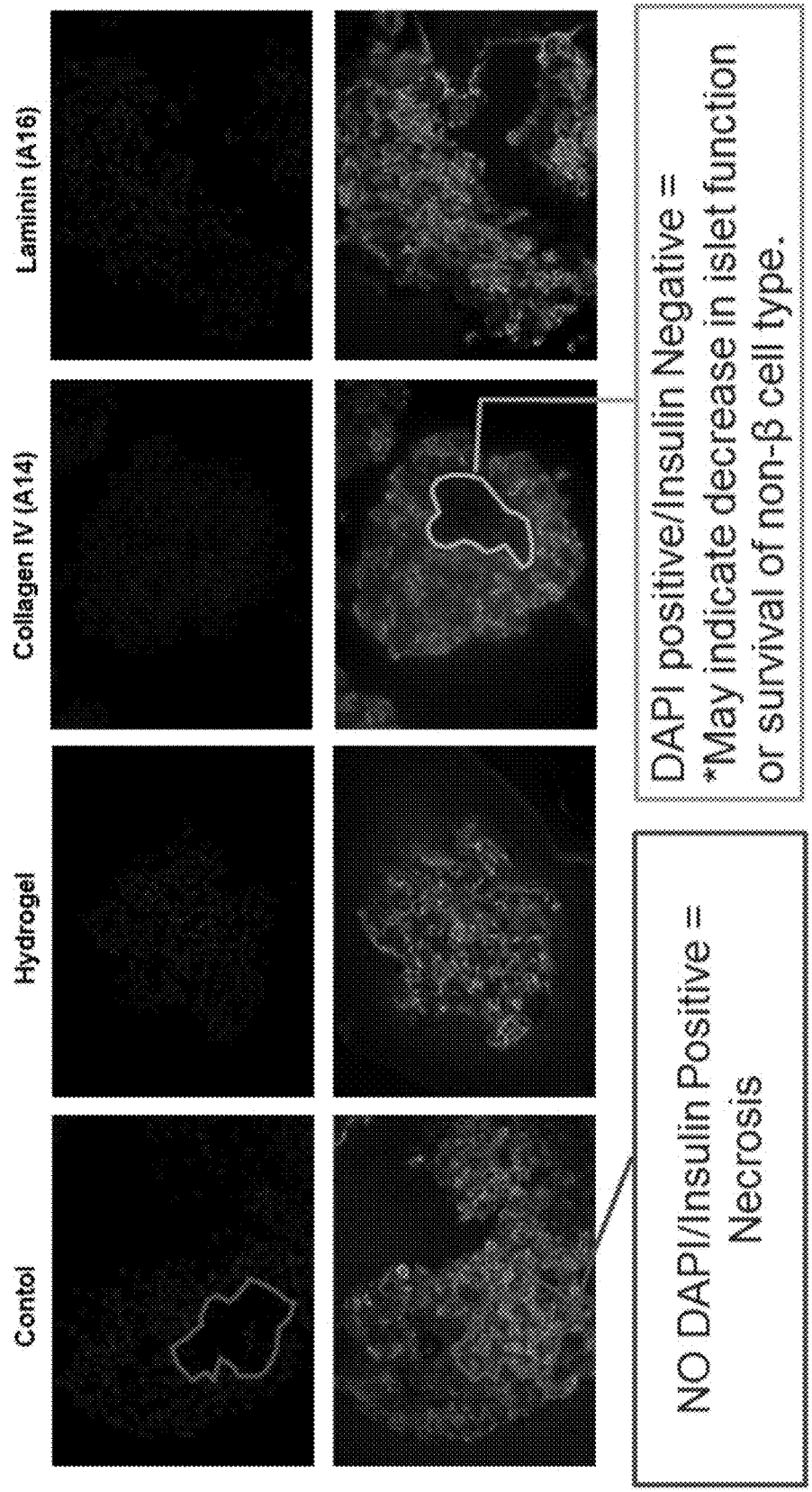
FIG. 21 provides that functionalized SP based hydrogel may prevent islet necrosis in vitro.

Transplantation of non-encapsulated islets in non-hepatic sites: Islets were isolated and suspended in a small volume of culture medium and injected to the submucosa of the stomach of LEW rats without success in reversing diabetes. Although different methods were used with the intent to distribute islets widely without clumping, histological examination revealed that non-encapsulated islets aggregated to form large clumps and developed necrosis as was observed after day 7 (see FIG. 8B). On the same slide, adjacent to the large necrotic aggregates, some single islets were found and stained insulin-positive. These results exemplify the need to develop a means to distribute islets separately and in thin layers to maintain viability and function in order to achieve diabetes reversal in extrahepatic sites.

Transplantation of hydrogel-encapsulated islets to extrahepatic sites: To examine the potential use of SP hydrogel for islet transplantation outside of the liver, islets encapsulated with SP hydrogel were placed in various extrahepatic sites, including under the kidney capsule, within the intestinal wall, in a pocket constructed in the omentum, and in subcutaneous sites of syngeneic recipients (see FIG. 6C). Contrary to the studies conducted without the use of hydrogel, encapsulated islets survived and stained positive for insulin at various time points in all these extraheptic sites. In addition, no tightly aggregated clumps were observed.

Finally, to evaluate the efficacy of encapsulated islets in lowering hyperglycemia, 500 syngeneic islets were transplanted with or without SP hydrogel in an omental pouch and monitored for diabetes reversal. Encapsulated islets functioned significantly better in reversing diabetes as compared to control islets (see FIG. 6D). From day 7 on, blood glucose levels of the hydrogel group were significantly lower than controls ($p<0.05$).

Figure 22:
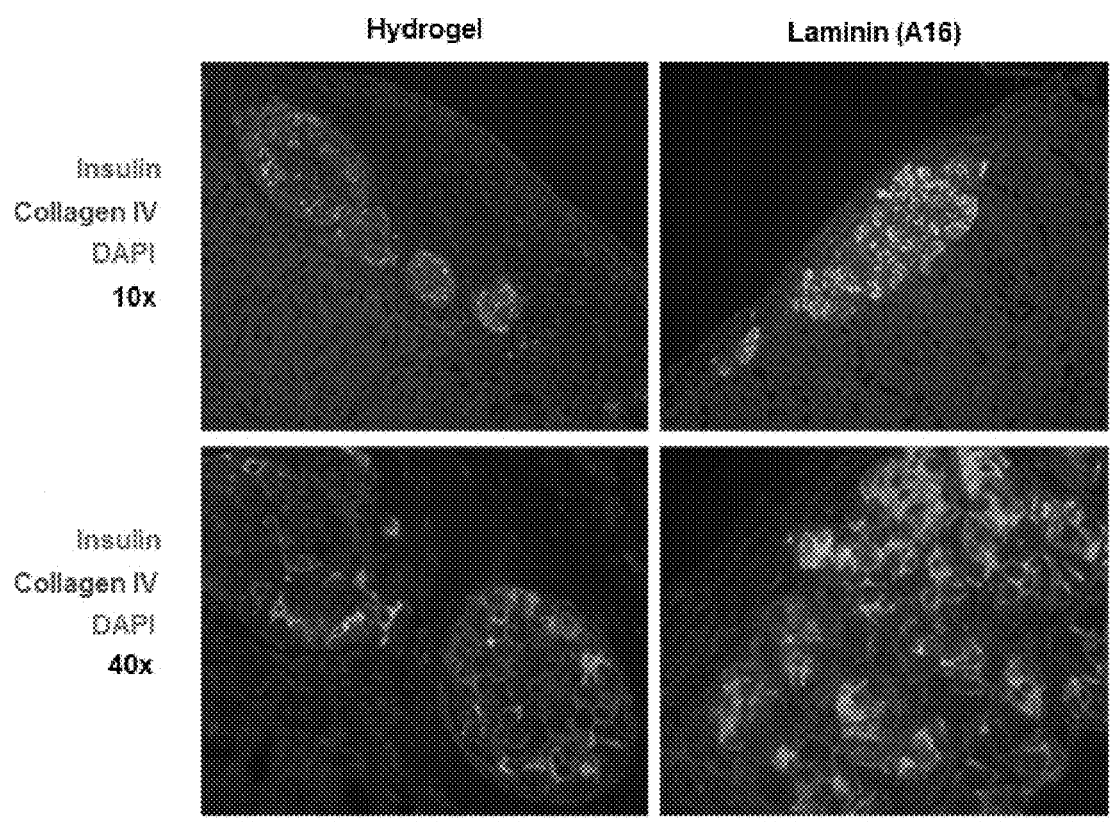
FIG. 22 provides that functionalized SP based hydrogel improves ECM reconstruction in vivo. Human islets were transplanted under the kidney capsule of non-diabetic NoD-scid mice. The images are from 15 days post transplantation.

In vivo luminescence imaging as a model to monitor subcutaneously transplanted Luc(+) islet viability. The viability of islets transplanted into the subcutaneous space was monitored by utilizing the Luc+ transgenic rat. Briefly, islets isolated from Luc(+) rats were hand-picked and resuspended in either a SP based hydrogel or transplant media which was then transplanted through a small incision on the ventral abdominal wall. Following transplantation, islet viability was measured through luciferase activity. On various days post-transplant, d-Luciferin was injected intra peritoneally. Results were obtained by creating fixed area region of interest (ROI) around the transplant site and a control site from which the photon counts in the ROIs were compared. The preliminary data indicate that while islets alone have an increased response to the luciferin initially, over time that response fades. The SP-hydrogel encapsulated islets maintain a higher response through the end of the experimental period (see FIG. 22), indicating higher viability for islets encapsulated within SP-hydrogel.

A number of embodiments have been described herein. Nevertheless, it will be understood that various modifications may be made without departing from the spirit and scope of this disclosure. Accordingly, other embodiments are within the scope of the following claims.

What is claimed is:

1. A hydrogel that is biodegradable and implantable in a subject comprising one or more polymers having a structure of Formula I and structure of Formula III:

which can be cross-linked under mild reaction conditions to form a plurality of crosslinks having the general structure of Formula V:

Formula I

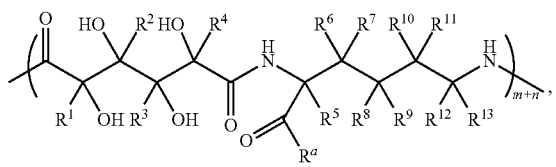

Formula III

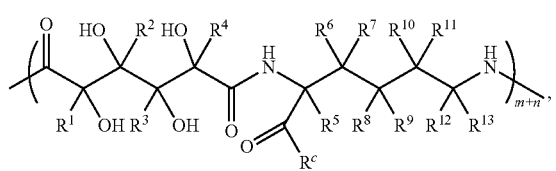

Formula V wherein m and n are integers greater than one;

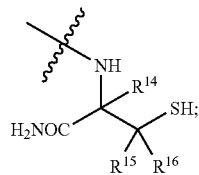

$R^a$ is independently an OH, or

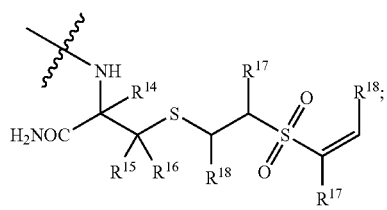

$R^c$ is independently a OH or $R^1$-$R^{18}$ are independently selected from the group consisting of H, optionally substituted ($C_{1-12}$)-alkyl, optionally substituted ($C_{1-12}$)-heteroalkyl, optionally substituted ($C_{1-12}$)-alkenyl, optionally substituted ($C_{1-12}$)-heteroalkynyl, optionally substituted ($C_{1-12}$)-alkynyl, optionally substituted ($C_{1-12}$)-heteroalkynyl, optionally substituted cylcoalkyl, optionally substituted cyclcoalkenyl, halide, alcohol, ketone, aldehyde, acyl halide, carbonate, carboxylic acid, ester, ether, amide, amine, imine, azide, cyanate, azo, nitrate, nitrile, nitro, nitroso, thiol, sulfide, disulfide, sulfoxide, sulfone, sulfinic acid, sulfonic acid, thiocyanate, thione, thial, phosphine, phosphonic acid, phosphate, phosphodiester, boronic acid, boronic ester, borinic acid, and borinic ester; and wherein one or more of the monomers of a polymer are chemically functionalized to comprise one or more cell signaling ligands and/or one or more cell signaling factors.

2. The hydrogel of claim 1, wherein the one or more cell signaling ligands and/or the one or more cell signaling factors are selected from the group consisting of cell adhesion ligands, growth factors, chemokines, cytokines, receptor tyrosine kinase ligands, JAK-STAT ligands, transforming growth factor ligands, tumor necrosis factor ligands, antigens of the T-cell receptor, steroid receptor ligands, pancreatic and duodenal homeobox gene 1, soluble factors, G-protein-coupled receptor ligands, and neurotransmitters.

3. The hydrogel of claim 1, wherein the hydrogel further comprises one or more biological materials and/or one or more pharmaceutical agents.

4. The hydrogel of claim 3, wherein the hydrogel comprises one or more cells.

5. The hydrogel of claim 4, wherein the one or more cells are encapsulated in the hydrogel in situ.

6. The hydrogel of claim 4, wherein the one or more cells are islets.

7. The hydrogel of claim 6, wherein the islets are of human origin.

8. A method of treating a disease or disorder in a subject comprising implanting a hydrogel of claim 3 at a site in the subject.

9. The method of claim 8, wherein the hydrogel is implanted at an extrahepatic site in the subject.

10. The method of claim 8, wherein the subject's disease or disorder can be treated by using cell therapy.

11. The method of claim 8, wherein implanting a hydrogel comprises in situ polymerization of the hydrogel, wherein one or more biological materials and/or one or more pharmaceutical agents are suspended in a solution comprising a polymer having a structure of Formula I and/or in a solution comprising a polymer having a structure of Formula II.

12. The method of claim 11, wherein islets are suspended in a solution comprising a polymer having a structure of Formula II.

13. The method of claim 8, wherein the disease or disorder to be treated is type 1 diabetes, and wherein islets are encapsulated in the hydrogel.

14. The hydrogel of claim 1, wherein the one or more cell signaling ligands and/or the one or more cell signaling factors are islet recognition motifs derived from laminin-α5 chain (Lm-α5) and collagen IV (Col IV).

15. The hydrogel of claim 14, wherein the islet recognition motifs are peptides which comprise the sequence of SEQ ID NO:1, SEQ ID NO:2, SEQ ID NO:3, SEQ ID NO:4, or SEQ ID NO:5.

16. The hydrogel of claim 14, wherein the hydrogel further comprises one or more biological materials and/or one or more pharmaceutical agents.

17. The hydrogel of claim 16, wherein the hydrogel comprises one or more cells.

18. The hydrogel of claim 17, wherein the one or more cells are encapsulated in the hydrogel in situ.

19. The hydrogel of claim 18, wherein the one or more cells are islets.

20. The hydrogel of claim 19, wherein the islets are of human origin.

21. The hydrogel of claim 19, wherein the hydrogel further comprises mesenchymal stem cells that over-express vascular endothelial growth factor.

22. A method of treating a disease or disorder in a subject comprising implanting a hydrogel claim 19 at a site in the subject.

23. The method of claim 22, wherein the hydrogel is implanted at an extrahepatic site in the subject.

24. The method of claim 23, wherein implanting a hydrogel comprises in situ polymerization of the hydrogel, wherein one or more biological materials and/or one or more pharmaceutical agents are suspended in a solution comprising a polymer having a structure of Formula I and/or in a solution comprising a polymer having a structure of Formula III.

25. The method of claim 24, wherein islets are suspended in a solution comprising a polymer having a structure of Formula III.

26. The method of claim 22, wherein the disease or disorder to be treated is type 1 diabetes, and wherein islets are encapsulated in the hydrogel.

27. The method of claim 26, wherein the implanted islets secrete insulin into the blood stream in response to elevated blood glucose levels or hyperglycemia in the subject.

28. The hydrogel of claim 1, wherein the polymers of the hydrogel comprise monomers that are chemically functionalized with two or more different cell signaling ligands and/or cell signaling factors.

29. The hydrogel of claim 1, wherein the monomers are chemically functionalized to comprise two or more cell signaling ligands and/or one or more cell signaling factors.

30. The hydrogel of claim 1, wherein the hydrogel comprises a density of cell signaling ligands and/or cell signaling factors from 0.05 mM to 5.0 mM.

* * * * *